(12) United States Patent
Wright et al.

(10) Patent No.: US 7,223,536 B2
(45) Date of Patent: May 29, 2007

(54) METHODS FOR DETECTING SINGLE NUCLEOTIDE POLYMORPHISMS

(75) Inventors: David J. Wright, Chapel Hill, NC (US); Maria A. Milla, Wynnewood, PA (US); James G. Nadeau, Chapel Hill, NC (US); G. Terrance Walker, Chapel Hill, NC (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 09/778,168

(22) Filed: Feb. 7, 2001

(65) Prior Publication Data

US 2001/0009761 A1    Jul. 26, 2001

Related U.S. Application Data

(62) Division of application No. 09/335,218, filed on Jun. 17, 1999, now abandoned.

(51) Int. Cl.
*C12Q 1/68* (2006.01)
*C12P 19/34* (2006.01)
*C07H 21/04* (2006.01)

(52) U.S. Cl. .................. 435/6; 435/91.2; 536/23.1; 536/24.3

(58) Field of Classification Search ............ 435/6, 435/91.2; 536/24.3
See application file for complete search history.

(56) References Cited

U.S. PATENT DOCUMENTS

| | | | | |
|---|---|---|---|---|
| 4,683,195 | A * | 7/1987 | Mullis et al. | 435/6 |
| 5,578,458 | A * | 11/1996 | Caskey et al. | 435/6 |
| 5,595,890 | A * | 1/1997 | Newton et al. | 435/91.2 |
| 5,763,184 | A * | 6/1998 | Reynolds et al. | 435/6 |
| 6,207,379 | B1 * | 3/2001 | Lee et al. | 435/6 |
| 6,326,145 | B1 * | 12/2001 | Whitcombe et al. | 435/6 |

FOREIGN PATENT DOCUMENTS

WO      WO 95/22626   *   8/1995

OTHER PUBLICATIONS

Guatelli et al. "Isothermal, invitro amplification of nucleic acids by a multienzyme reaction modeled after retrovrial replication" Proc. Natl. Acad. Sci. USA, 1990, 87: 1874-1878.*

Chen et al. "Template-directed dye-terminator incorporation assay: a homogenous DNA diagnostic method based on fluorescence resonacne energy transfer" Nucleic Acids Research, 1997, 25(2): 347-353.*

Walker et al. "Strand displacement amplification-an isothermal invitro DNA amplification technique" Nucleic Acids Research, 1992, 20(7): 1691-1696.*

Kruasa et al. "Defining the allelic variants of HLA-A30 in the Sardinian population using amplification refractorymutation systems-polymerase chain reaction" Human Immunology, 1995, 44: 35-42.*

Fauser et al Simultaneous detection fo multiple point mutataions using gluorescence-coupled competetive primer extension, BioTechniques, 1997, 22(5): 964-968.*

Ugozzoli et al., 1991, *Methods: A Companion to Methods in Enzymology* 2:42-48.

Kwok et al., 1990, *Nucleic Acids Research* 18:999-1005.

Kwok et al., 1994, *PCR Methods and Amplifications* 3:S:39-47.

* cited by examiner

*Primary Examiner*—B J Forman
(74) *Attorney, Agent, or Firm*—Allan M. Kiang

(57) ABSTRACT

The present invention provides methods for detecting and identifying sequence variations in a nucleic acid sequence of interest using a detector primer. It has been found that the reduced efficiency of primer extension by DNA polymerases when the 3' end of a primer does not hybridize perfectly with the target can be adapted for use as a means for distinguishing or identifying the nucleotide in the target which is at the site where the diagnostic mismatch between the detector primer and the target occurs. The detector primer hybridizes to the sequence of interest and is extended with polymerase. The efficiency of detector primer extension is detected as an indication of the presence and/or identity of the sequence variation in the target. The inventive methods make use of nucleotide mismatches at or near the 3' end of the detector primer to discriminate between the nucleotide sequence of interest and a second nucleotide sequence which may occur at that same site in the target. The methods are particularly well suited for detecting and identifying single nucleotide differences between a target sequence of interest (e.g., a mutant allele of a gene) and a second nucleic acid sequence (e.g., a wild type allele for the same gene).

54 Claims, 18 Drawing Sheets

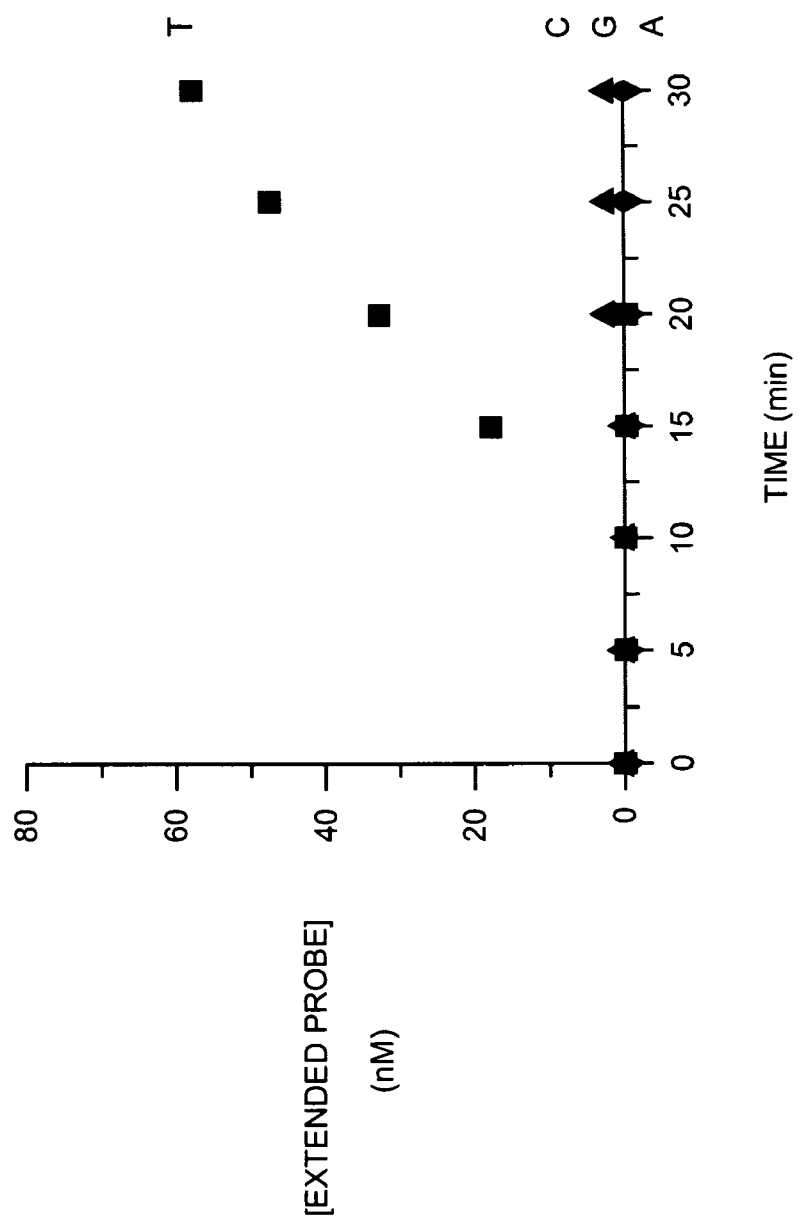
FIG. 1A -3A/3'A DETECTOR PROBE

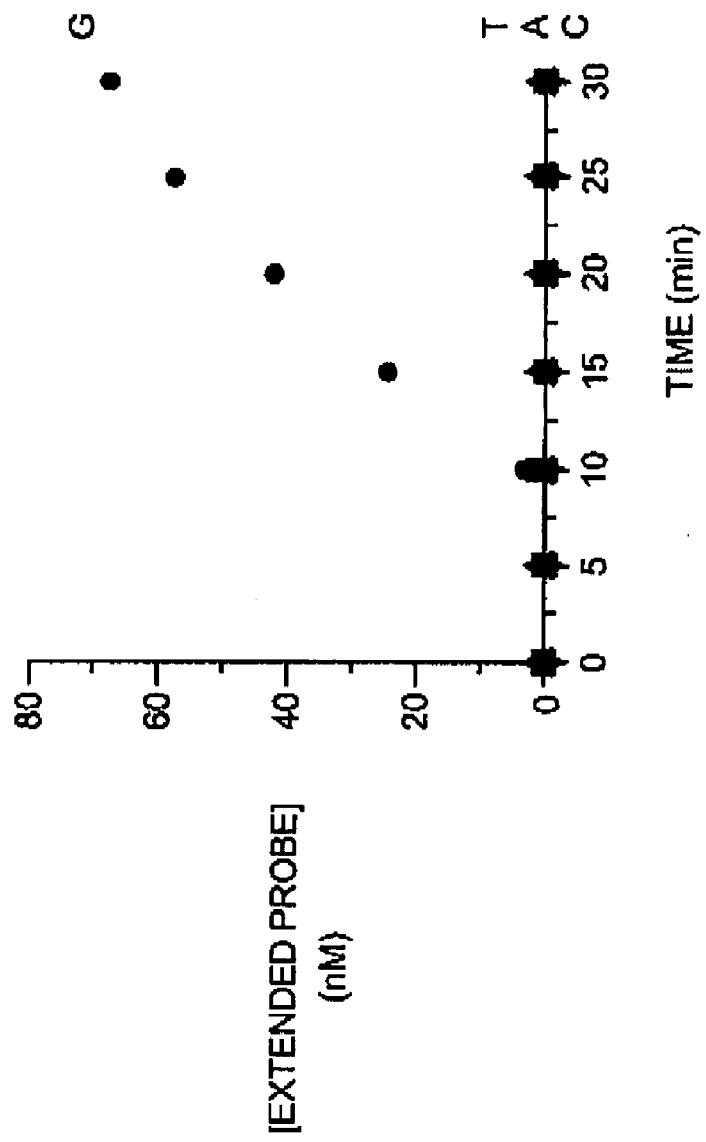
FIG. 1B 3A/3'C DETECTOR PROBE

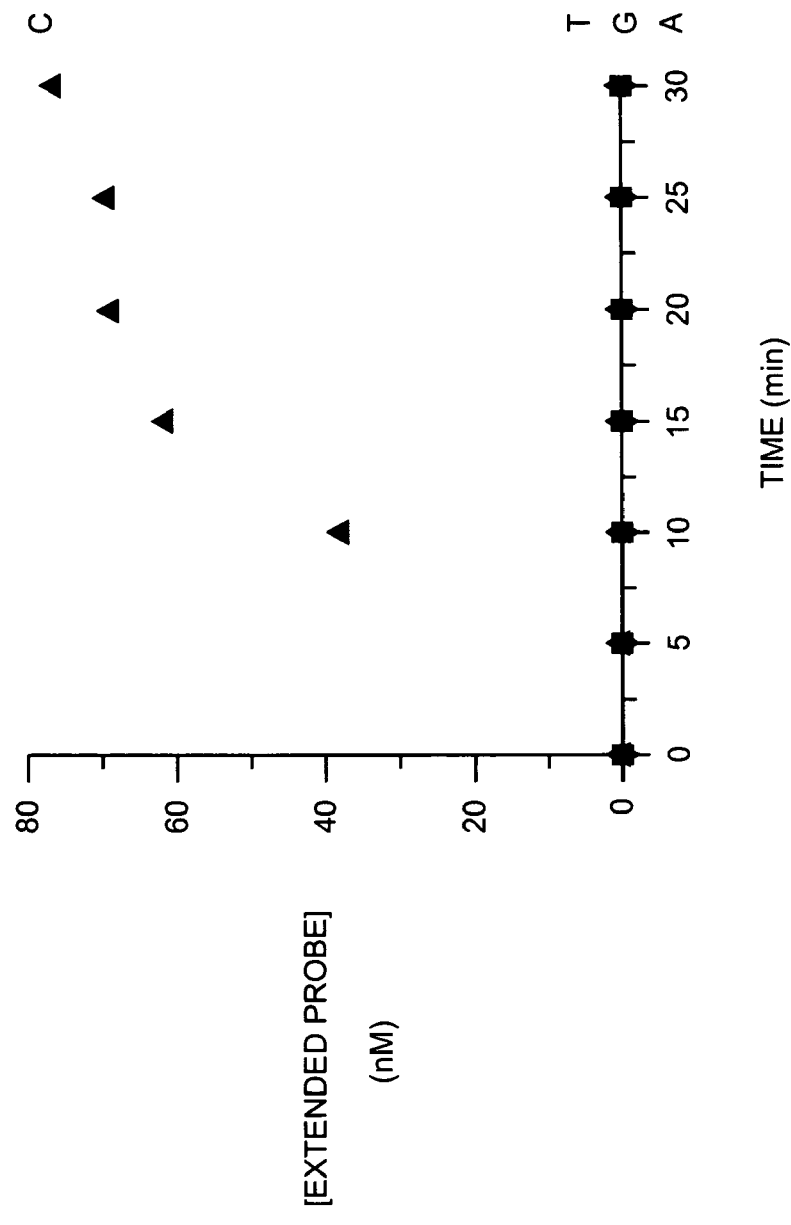
FIG. 1C -3A/3'G DETECTOR PROBE

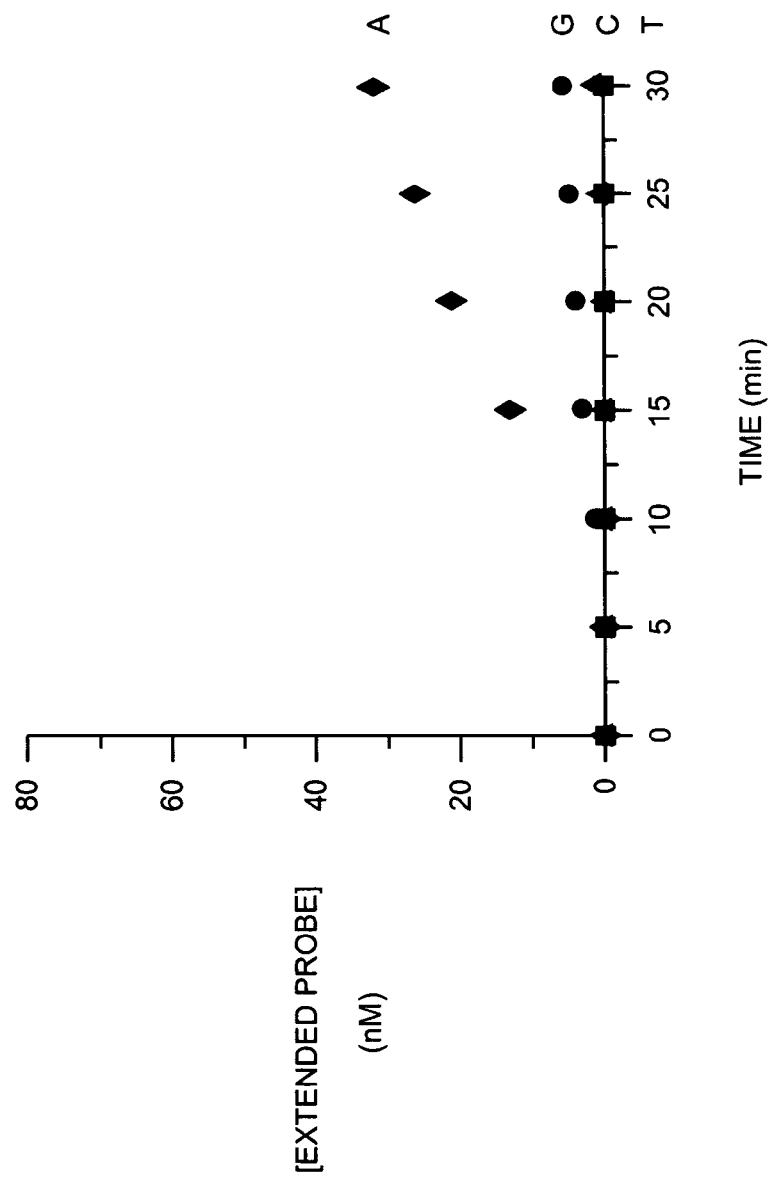
FIG. 1D -3A/3'T DETECTOR PROBE

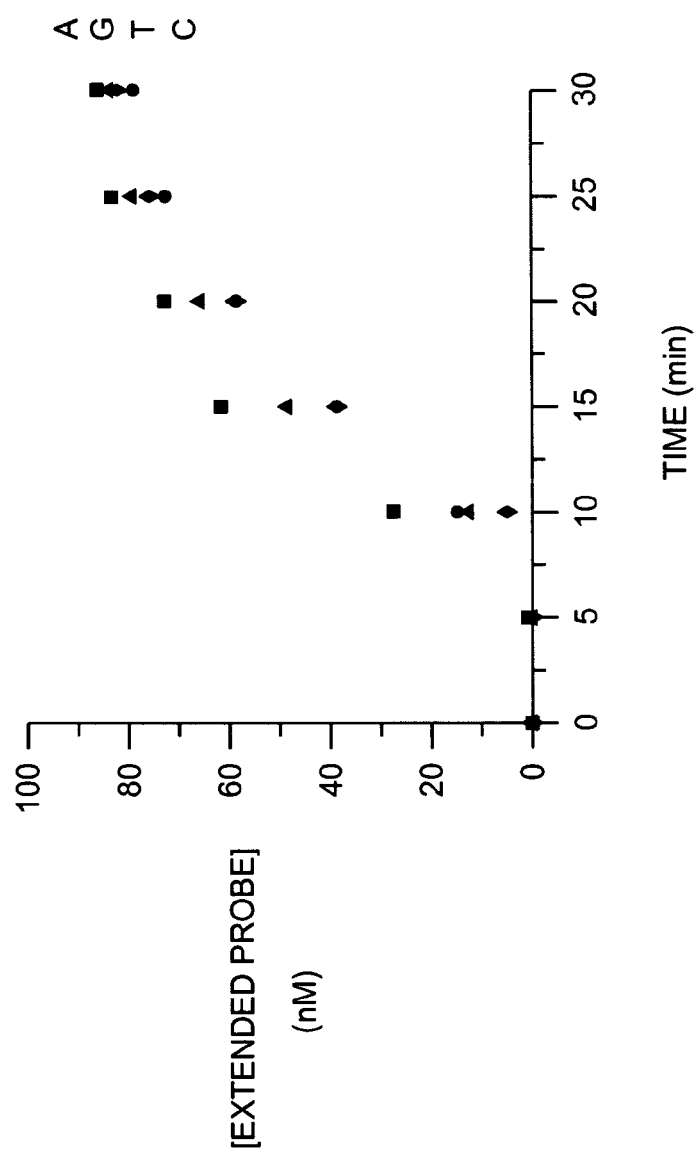
FIG. 1E  S1.1/2.2 SDA WITH 10,000 A, C, G, OR T TARGETS

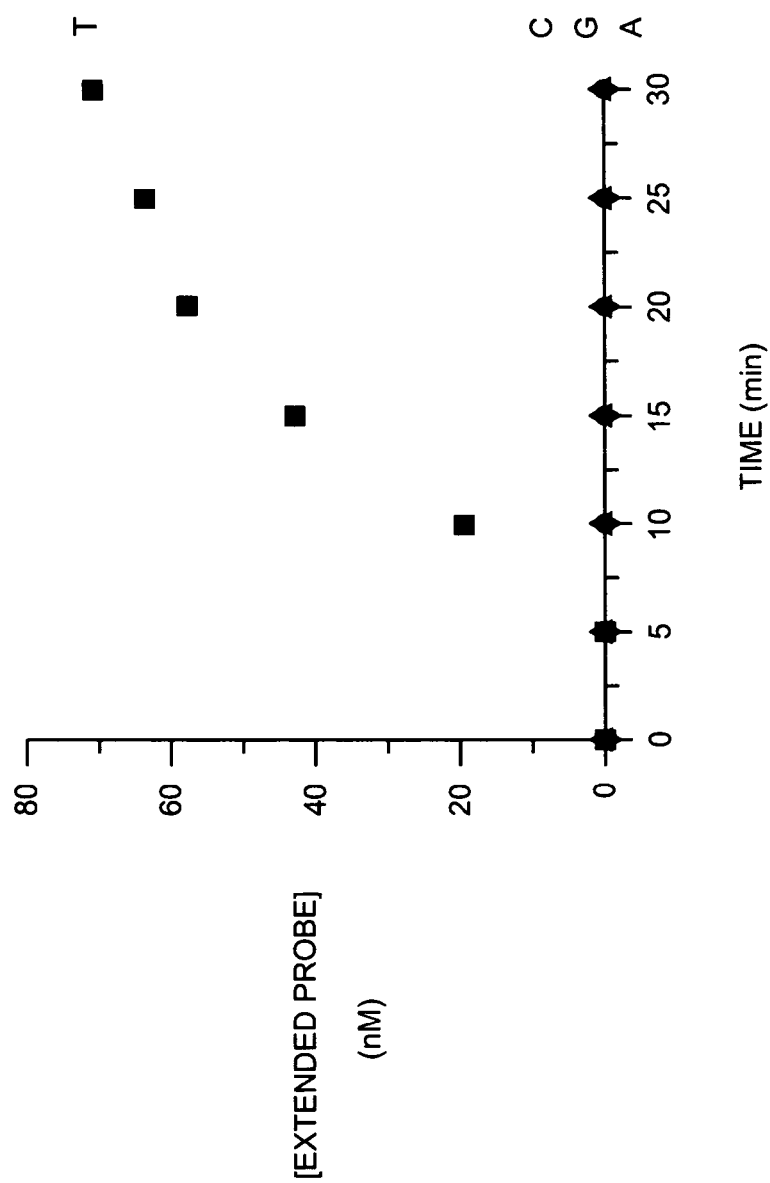

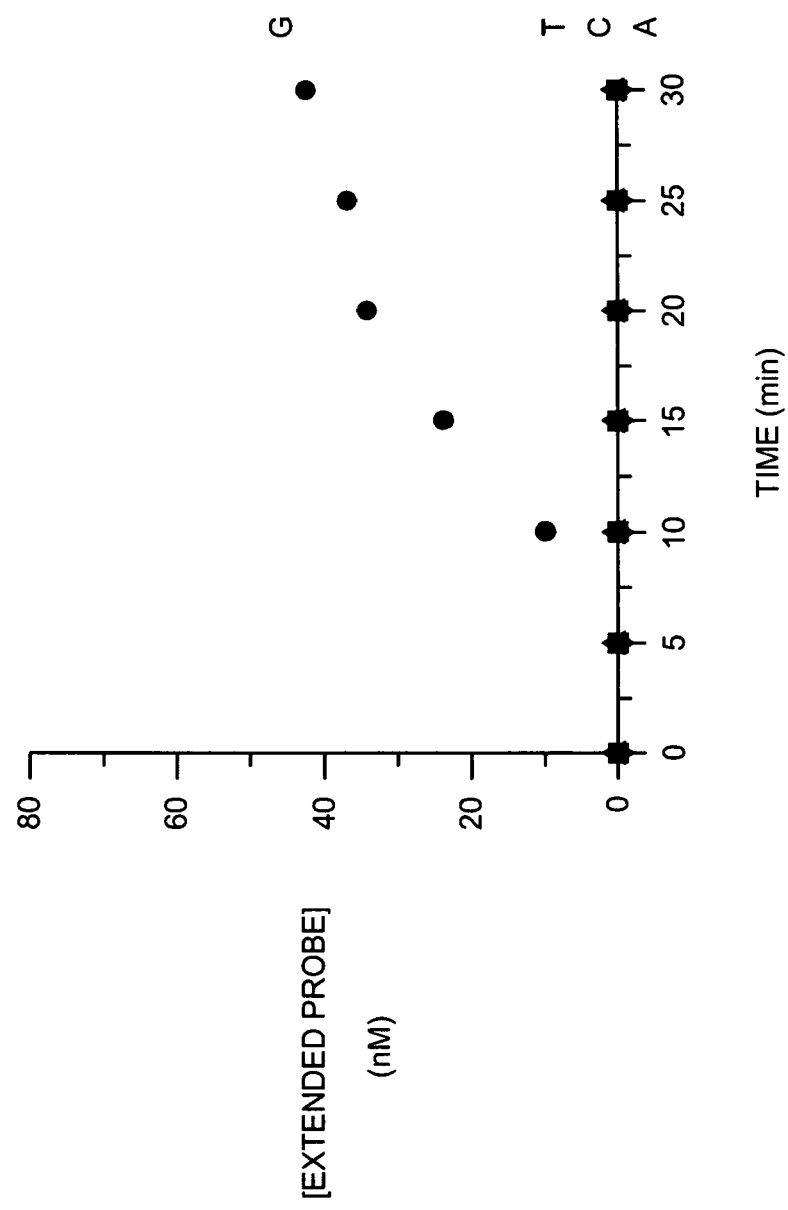
FIG. 2B -1C DETECTOR PROBE

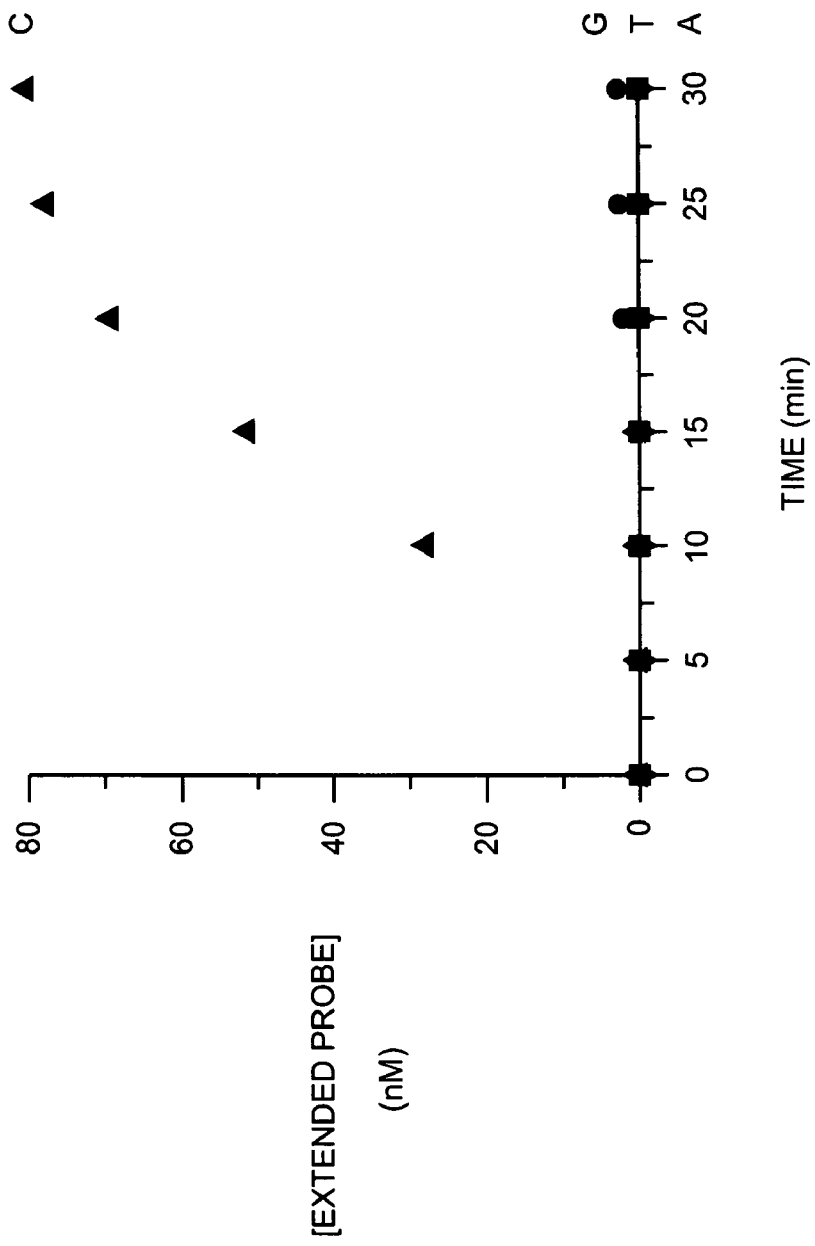
FIG. 2C -1G DETECTOR PROBE

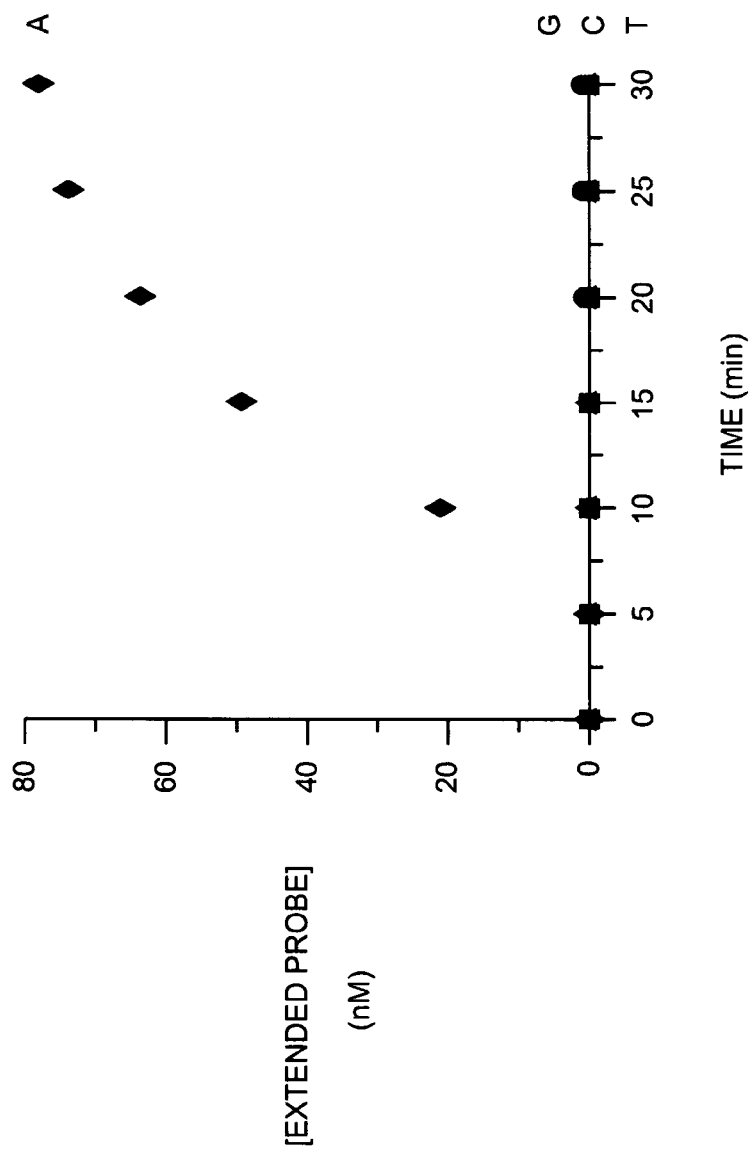
FIG. 2D -1T DETECTOR PROBE

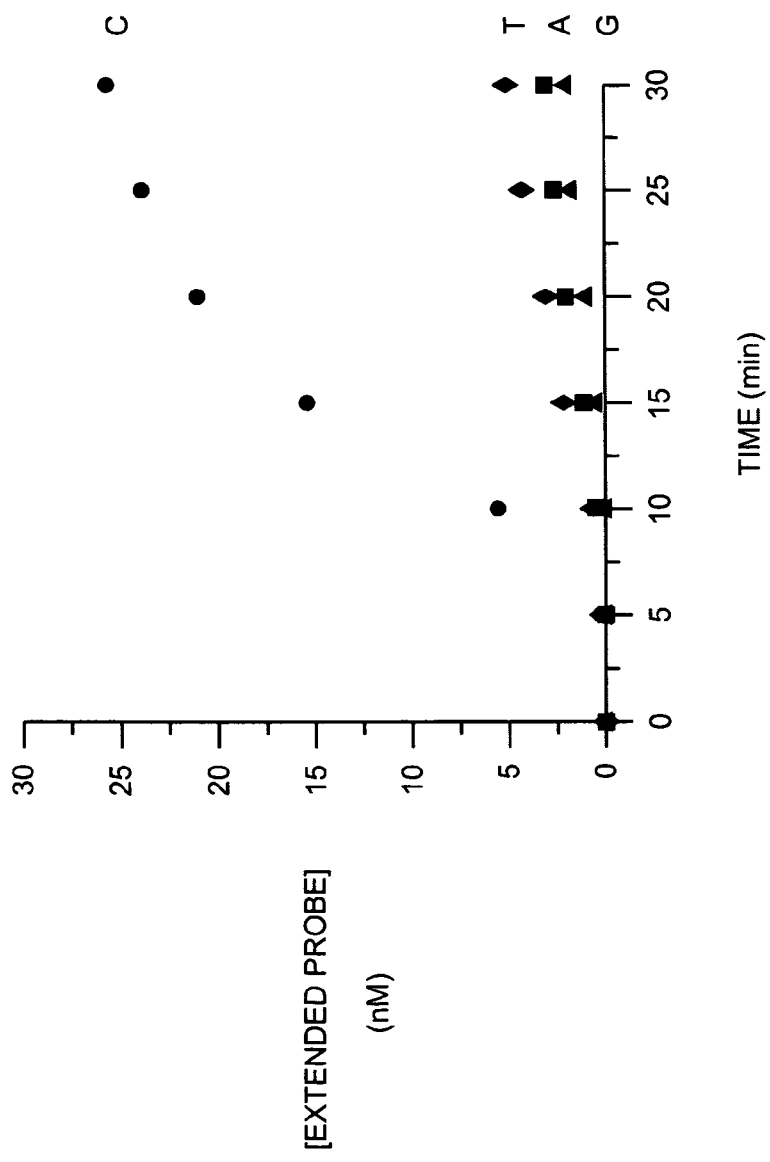
FIG. 2E  NP-6 DETECTOR PROBE IN SDA WITH 10,000 A, C, G, OR T TARGETS

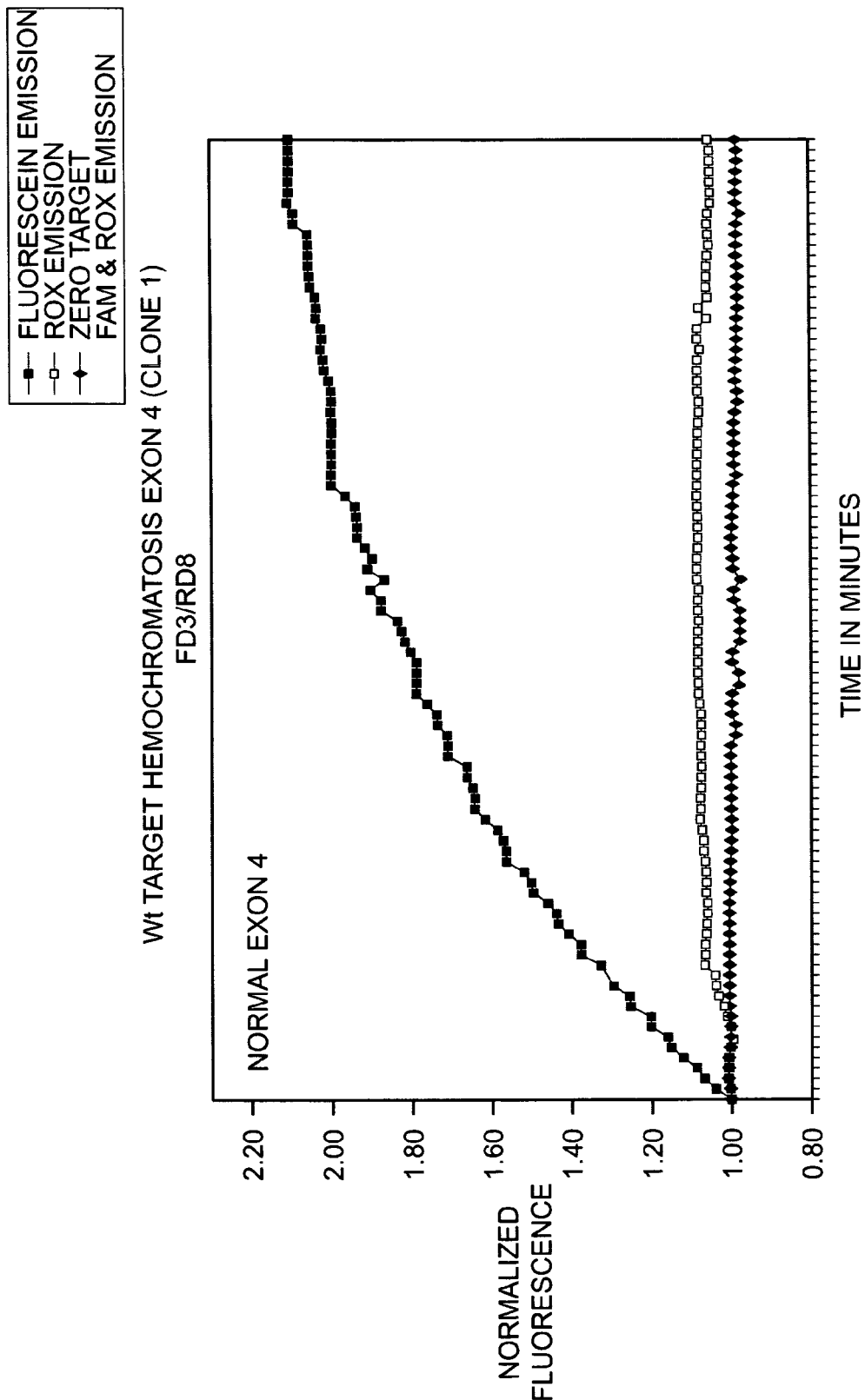
FIG. 3A  TWO-COLOR ALLELE ANALYSIS ON PROBE TEC

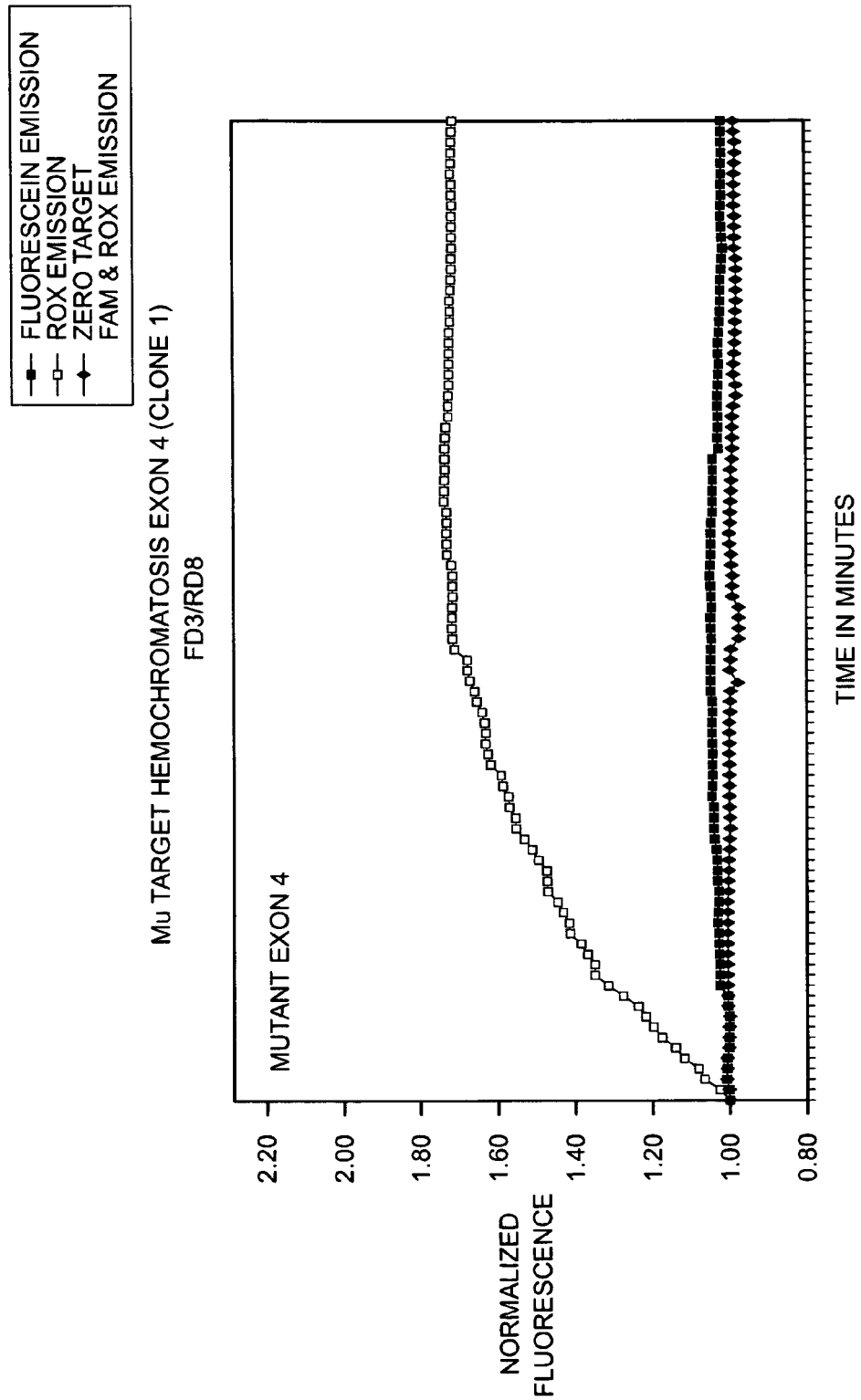
FIG. 3B  TWO-COLOR ALLELE ANALYSIS ON PROBE TEC

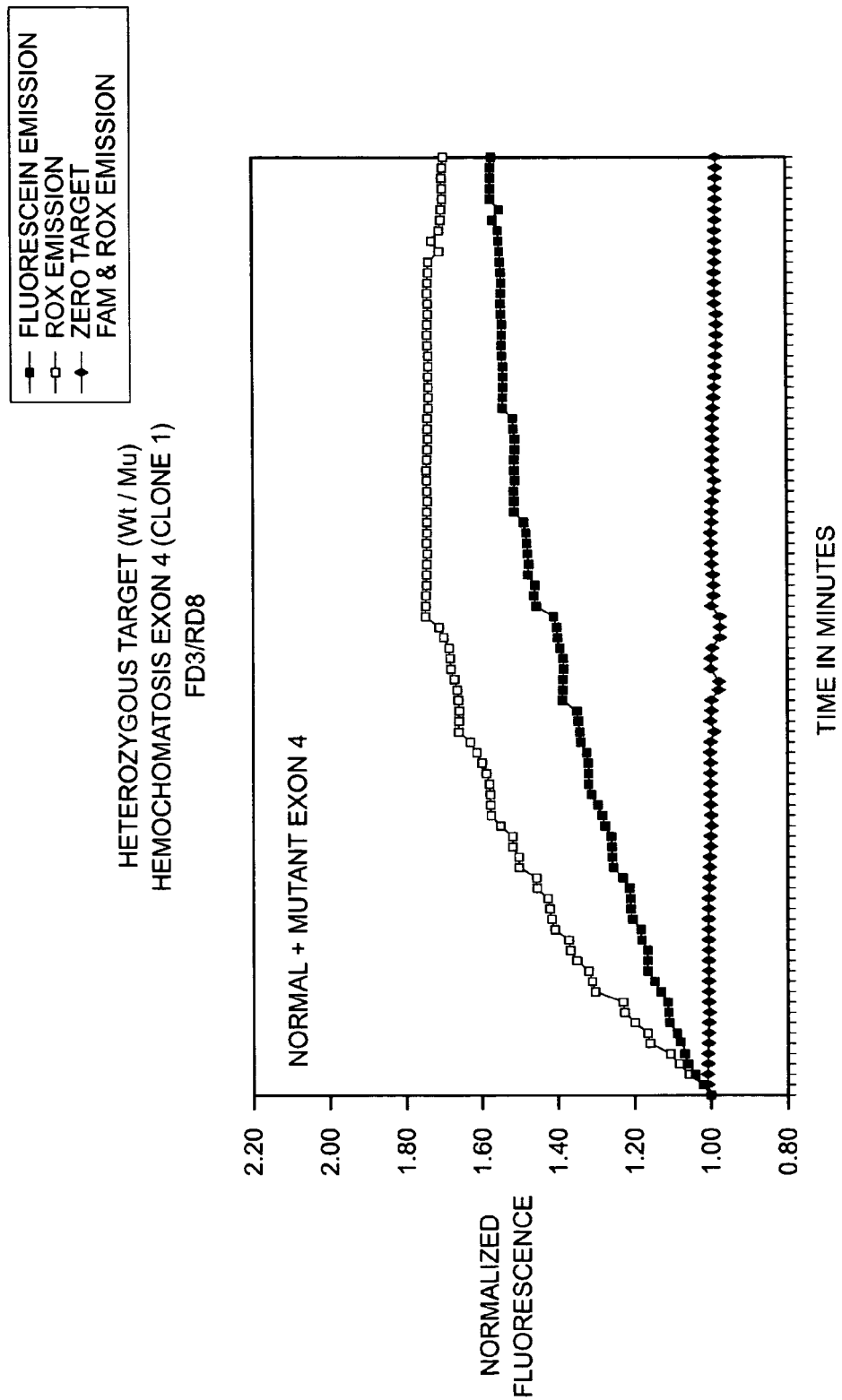
FIG. 3C  TWO-COLOR ALLELE ANALYSIS ON PROBE TEC

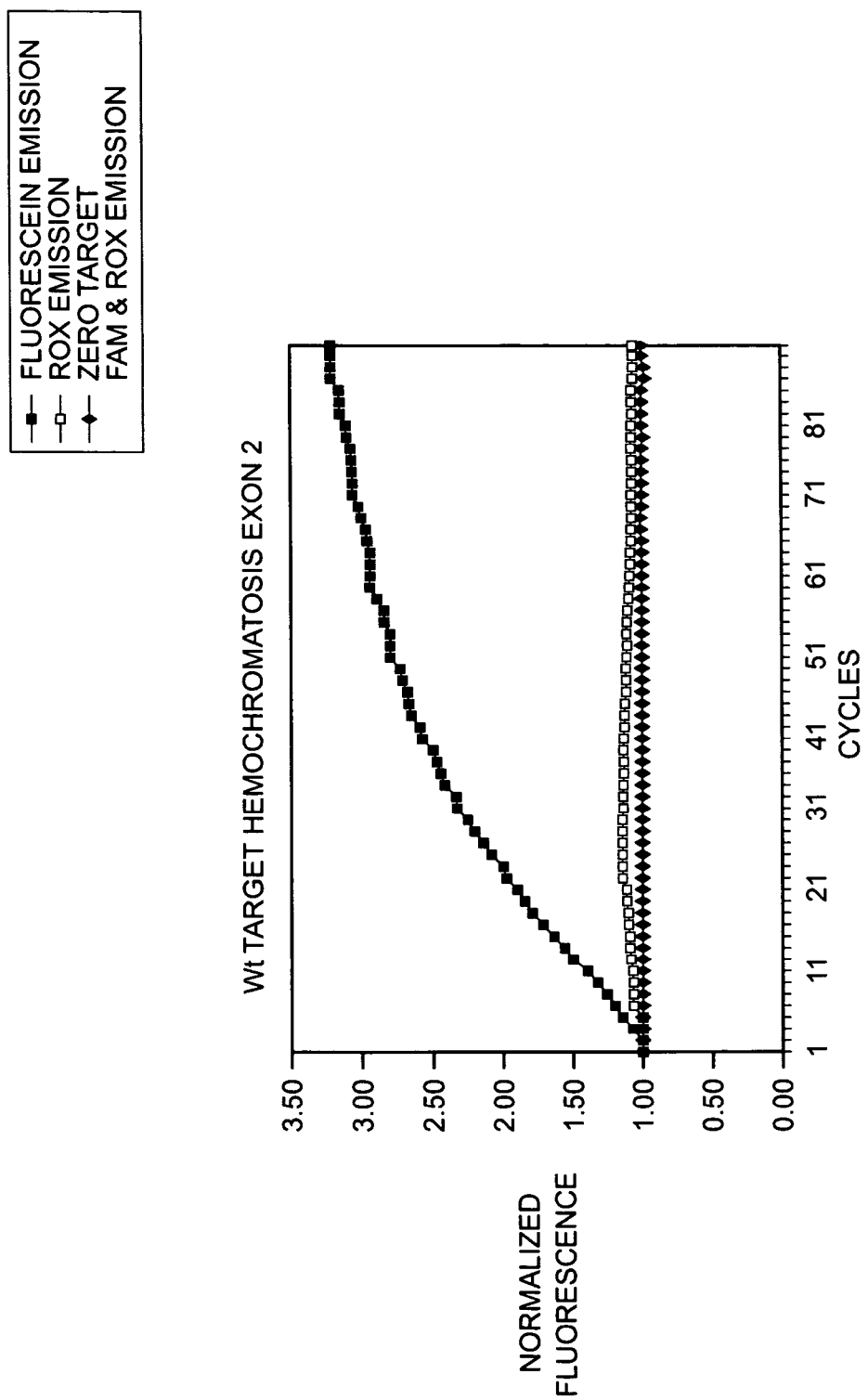
FIG. 4A  TWO-COLOR SNP ANALYSIS ON PROBE TEC

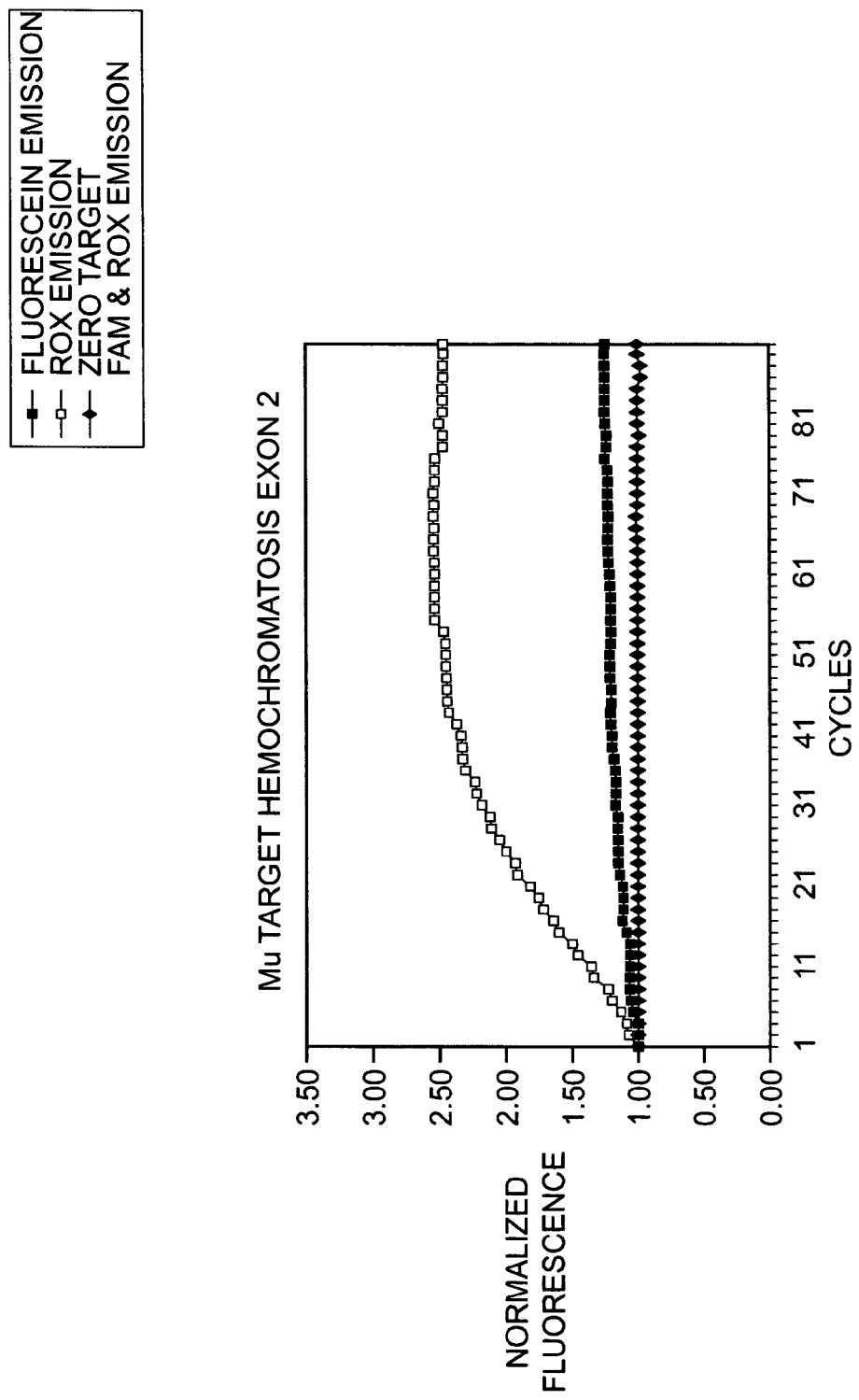
FIG. 4B  TWO-COLOR SNP ANALYSIS ON PROBE TEC

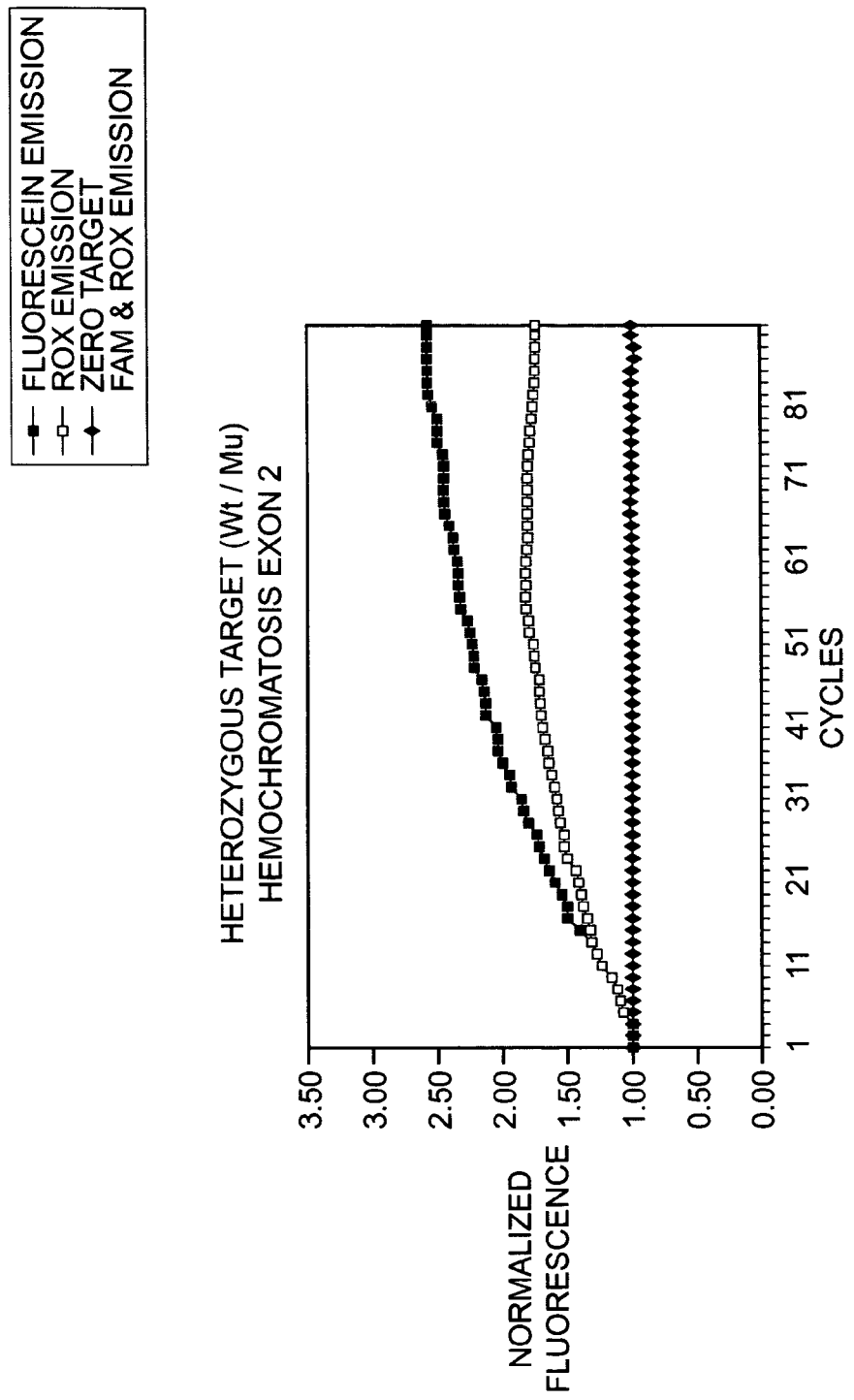
FIG. 4C TWO-COLOR SNP ANALYSIS ON PROBE TEC

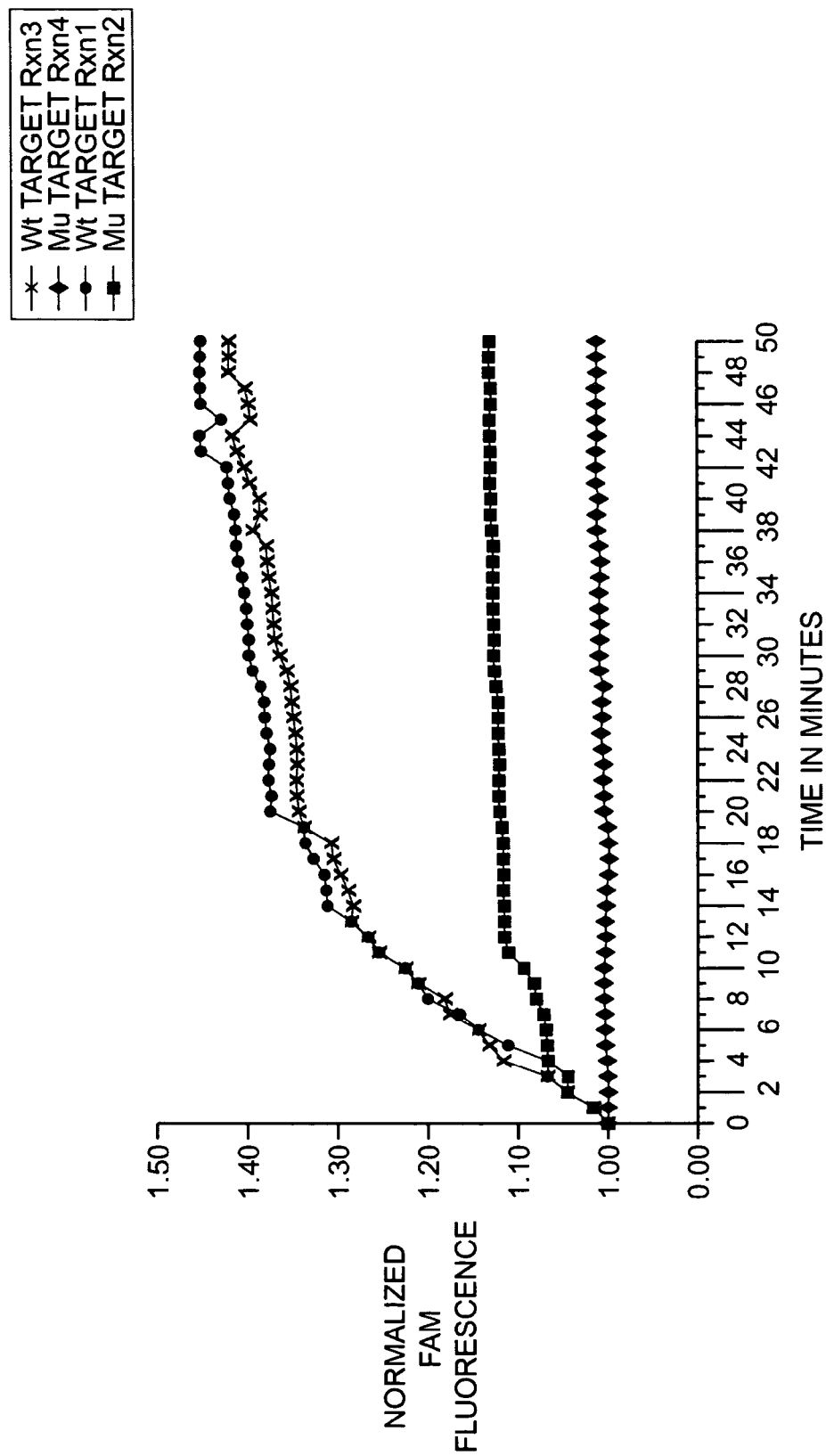
FIG. 6    SDA HH4 SYSTEM 105 TARGETS, FAM DETECTOR PROBES AT 300 nM

METHODS FOR DETECTING SINGLE NUCLEOTIDE POLYMORPHISMS

This application is a division of prior application Ser. No. 09/335,218, filed Jun. 17, 1999 now abandoned.

FIELD OF THE INVENTION

The present invention relates to methods for detecting and identifying sequence variations in nucleic acids.

BACKGROUND OF THE INVENTION

Detecting and identifying variations in DNA sequences among individuals and species has provided insights into evolutionary relationships, inherited disorders, acquired disorders and other aspects of molecular genetics. Analysis of sequence variation has routinely been performed by analysis of restriction fragment length polymorphism (RFLP) which relies on a change in restriction fragment length as a result of a change in sequence. RFLP analysis requires size-separation of restriction fragments on a gel and Southern blotting with an appropriate probe. This technique is slow and labor intensive and cannot be used if the sequence change does not result in a new or eliminated restriction site.

More recently, PCR has been used to facilitate sequence analysis of DNA. For example, allele-specific oligonucleotides have been used to probe dot blots of PCR products for disease diagnosis. If a point mutation creates or eliminates a restriction site, cleavage of PCR products may be used for genetic diagnosis (e.g., sickle cell anemia). General PCR techniques for analysis of sequence variations have also been reported. S. Kwok, et al. (1990. *Nucl. Acids Res.* 18:999-1005) evaluated the effect on PCR of various primer-template mismatches for the purpose of designing primers for amplification of HIV which would be tolerant of sequence variations. The authors also recognized that their studies could facilitate development of primers for allele-specific amplification. Kwok, et al. report that a 3' terminal mismatch on the PCR primer produced variable results. In contrast, with the exception of a 3' T mismatch, a 3' terminal mismatch accompanied by a second mismatch within the last four nucleotides of the primer generally produced a dramatic reduction in amplification product. The authors report that a single mismatch one nucleotide from the 3' terminus (N-1), two nucleotides from the 3' terminus (N-2) or three nucleotides from the 3' terminus (N-3) had no effect on the efficiency of amplification by PCR. C. R. Newton, et al. (1989. *Nucl. Acids Res.* 17:2503-2516) report an improvement in PCR for analysis of any known mutation in genomic DNA. The system is referred to as Amplification Refractory Mutation System or ARMS and employs an allele-specific PCR primer. The 3' terminal nucleotide of the PCR amplification primer is allele specific and therefore will not function as an amplification primer in PCR if it is mismatched to the target. The authors also report that in some cases additional mismatches near the 3' terminus of the amplification primer improve allele discrimination.

SUMMARY OF THE INVENTION

The present invention provides methods for detecting and identifying sequence variations in a nucleic acid sequence of interest using a detector primer. The detector primer hybridizes to the sequence of interest and is extended by polymerase if the 3' end hybridizes efficiently with the target. The methods are particularly well suited for detecting and identifying single nucleotide differences between the target sequence being evaluated (e.g., a mutant allele of a gene) and a second nucleic acid sequence (e.g., a wild type allele for the same gene), as they make use of nucleotide mismatches at or near the 3' end of the detector primer to discriminate between a first nucleotide and a second nucleotide which may occur at that site in the target. It has been found that the reduced efficiency of primer extension by DNA polymerases when one or more nucleotides at or near the 3' terminus of a primer do not efficiently hybridize with the target can be adapted for use as a means for distinguishing or identifying a nucleotide in the target which is at the site where the one or more nucleotides of the detector primer hybridize. The efficiency of the extension reaction for a selected detector primer hybridized to a selected target is monitored by determining the relative amount of extended detector primer which is produced in the extension reaction.

DESCRIPTION OF THE DRAWINGS

FIGS. 1A, 1B, 1C, 1D and 1E show the results of Example 1 for detection and identification of SNP's using a model target system and detector primers with a diagnostic 3' terminal nucleotide and a nondiagnostic mismatch at N-3.

FIGS. 2A, 2B, 2C, 2D and 2E show the results of Example 2 for detection and identification of SNP's using a model target system and detector primers with a diagnostic nucleotide at N-1 and no nondiagnostic mismatch.

FIGS. 3A, 3B and 3C show the results of Example 3 for real-time simultaneous detection and identification of two alleles of exon 4 of the HFE gene.

FIGS. 4A, 4B and 4C show the results of Example 4 for real-time simultaneous detection and identification of two alleles of exon 2 of the HFE gene.

FIG. 6 shows the results of Example 5, comparing the performance of multiple detector primers in reactions when the multiple detector primers have the same or different 5' tail sequences.

DETAILED DESCRIPTION OF THE INVENTION

Figure 5:
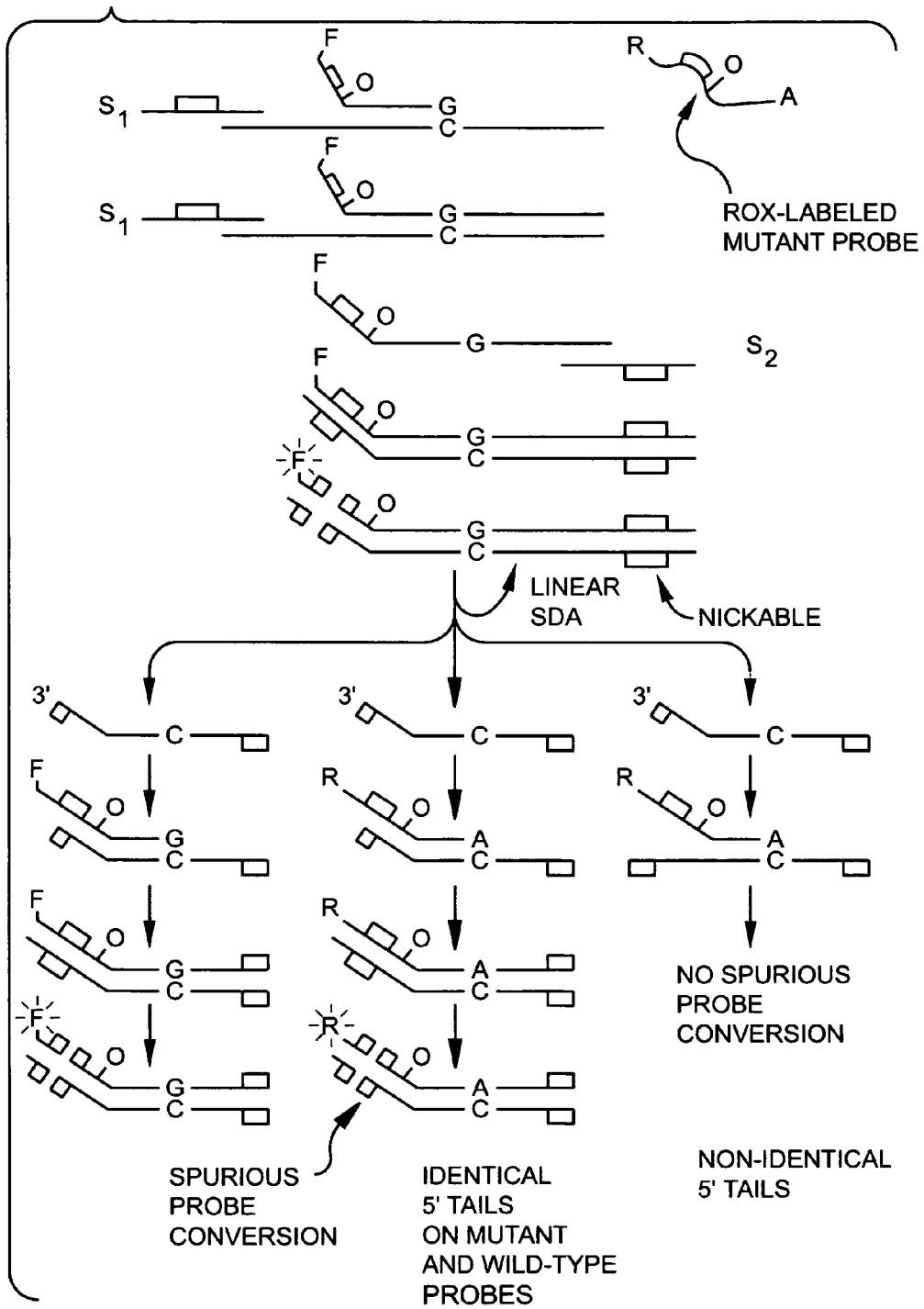
FIG. 5 illustrates a possible mechanism for generation of false-positive signals when multiple detector primers in an amplification reaction have the same 5' tail sequence.

The methods of the invention are useful for detecting variants of a nucleic acid sequence contained in a target nucleic acid. In particular, the methods of the invention are directed to detecting single nucleotide polymorphisms (SNPs) in a nucleic acid sequence of interest (e.g., alleles) and, optionally, to identifying such SNPs or alleles. Such nucleotide sequence variants may be detected directly in a sample to be analyzed during amplification of the target sequence. The inventive methods are based upon the relative inefficiency of primer extension by DNA polymerases when there are mismatches at or near the 3' end of a primer hybridized to an otherwise complementary sequence. Applicants have found that by selecting nucleotides at or near the 3' end of a detector primer such that one or more mismatches will occur when the detector primer is hybridized to a first allele of a target nucleic acid and correct base pairing will occur when the detector primer is hybridized to a second allele of the target nucleic acid, the difference in the efficiency of polymerase extension when the detector primer is hybridized to the two different alleles may be used to indicate which allele the target nucleic acid contains. When any one of multiple alleles may be present, multiple detector primers are employed in the analysis, each with a different potential mismatch at or near the 3' end. The detector primer which is most efficiently extended provides the identity of the allele (i.e., the identity of the nucleotide present in the target sequence being analyzed). For example, if a set of detector primers comprising A, G, C and T at the site of the allele to be identified is hybridized to the target of interest and extended, the identity of the allele will be the complement of the nucleotide in the signal primer which was most efficiently extended by the polymerase. For identification of the allele in a single reaction, multiple detector primers are present in the reaction and each of the detector primers has a separately detectable label associated with it (e.g., different fluorophores which can be distinguished within the mixture of detector primers).

More specifically, the detector primers of the invention are oligonucleotides which hybridize to the target sequence of interest and are extended by DNA polymerase during the isothermal amplification reaction. The nucleotide sequence of the detector primer is selected such that it hybridizes specifically to the target nucleic acid of interest and the majority of the detector primer base-pairs correctly in typical Watson-Crick fashion with the target. However, the nucleotide sequence of the detector primer at or near the 3' end is selected to discriminate between different SNPs or alleles of the target sequence (the diagnostic nucleotide position). The diagnostic nucleotide is defined as the nucleotide in the detector primer which allows analysis (e.g., presence or identification) of a particular allele in a selected target. That is, the sequence of the 3' end of the detector primer is selected such that hybridization with a first single nucleotide variation of the target sequence (e.g., a wild-type or mutant allele of a gene) results in correct Watson-Crick base-pairing at the site of the SNP and hybridization of the detector primer with a target containing a second single nucleotide variation of the target sequence at the same site (e.g., a second mutant allele of the gene) results in a mismatch between the detector primer and the target. As an example of how mismatches in the primer allow allele discrimination in amplification reactions, if a detector primer having a C residue at the diagnostic nucleotide position produces a high signal indicative of efficient extension of the detector primer, this indicates that the target allele is G. In contrast, low signal for the extended detector primer indicates that the target allele is not G. Use of a single detector primer to make the analysis allows identification of an allele if only one SNP is expected to occur in the target. If there may be multiple different alleles present at the same nucleotide position, a single detector primer will provide information on the presence or absence of the allele for which the detector primer is diagnostic. To identify the allele when multiple SNPs are possible, multiple detector primers containing A, T and G at the site of the SNP may be used to identify the allele in the target, i.e., the detector primer which produces a high signal associated with detector primer extension product contains the nucleotide which is the complement of the SNP in the target. In the present invention, the potentially mismatched nucleotide of the detector primer is placed at the 3' terminus or about one to four nucleotide residues from the 3' terminus (i.e., at the N, N-1, N-2, N-3 or N-4 position).

It has also unexpectedly been found that in many cases it is preferable to place a second mismatch in the sequence of the detector primer which is not directed to detection or identification of the allele of interest. The second, nondiagnostic mismatch often improves the level of discrimination between the SNPs being detected or identified and is preferably selected based on a region of the target sequence which is not expected to vary so that the nondiagnostic mismatch will occur regardless of the target allele being analyzed. The second mismatch may occur at any site within the detector primer which produces a positive effect on allele discrimination, but typically produces the greatest improvement when it is near the diagnostic nucleotide. This is typically within one to fifteen nucleotides from the diagnostic nucleotide, but preferably within about 1-5 nucleotides of the diagnostic nucleotide of the detector primer. Applicants believe that the second, nondiagnostic mismatch has a positional effect rather than a general effect on the $T_m$ of the detector primer, based on the observation that as the nondiagnostic mismatch is moved away from the diagnostic mismatch its positive effect on allele discrimination diminishes. Those skilled in the art are capable of determining through routine experimentation the appropriate placement of the nondiagnostic mismatch in a detector primer by evaluating its effect on allele discrimination using the detector primer.

Although it is known that a mismatch in a shorter oligonucleotide will have a greater effect on hybridization than a mismatch in a longer oligonucleotide, allele discrimination using the detector primers of the invention cannot be attributed entirely to a $T_m$-associated hybridization effect. For example, moving the position of the diagnostic nucleotide away from the 3' end of the detector primer toward the center of the molecule substantially reduces discrimination. If the sole mechanism of discrimination between alleles was $T_m$-associated hybridization efficiency, this repositioning should increase rather than decrease allele discrimination. We have observed the opposite, i.e., that the best allele discrimination occurs when the diagnostic nucleotide is near the 3' end of the detector primer. In addition, we have observed that detector primers which contain a diagnostic mismatch which is not at the 3' terminus and an additional nondiagnostic mismatch as described below provide good allele discrimination in relatively longer detector primers where simple differences in hybridization efficiency between matched and mismatched detector primers are expected to be minimal. The fact that the nondiagnostic nucleotide improves discrimination when located near the diagnostic nucleotide and has little effect when placed greater than fifteen nucleotides away further suggests that factors in addition to modification of hybridization efficiency are involved in allele discrimination according to the invention.

The detector primers of the invention are typically about 12-50 nucleotides in length. When only a diagnostic nucleotide is present, the detector primer is preferably about 12-24 nucleotides long, more preferably about 12-19 nucleotides long. For detector primers containing both a diagnostic and a nondiagnostic nucleotide, lengths of about 12-50 nucleotide are preferred, 15-36 nucleotides are more preferred and 18-24 nucleotides are most preferred.

The detector primers may be employed in a variety of ways in the isothermal amplification methods of the invention. In a first embodiment, the detector primer may be an amplification primer for use in a nucleic acid amplification reaction. That is, the detector primer may perform two functions in the amplification reaction—amplification of the target sequence of interest and detection or identification of SNPs within the target sequence (a "detector/amplification primer"). The structure and function of amplification primers for SDA, 3SR, NASBA, TMA and other isothermal amplification reactions are well known in the art and it is within the ordinary skill in the art to adapt these amplification primers for use as detector primers in the present invention by selecting the 3' nucleotide sequence as taught herein. For PCR, no special sequences or structures are required in the amplification primer to drive the amplification reaction. For this reason, amplification primers for PCR generally consist only of target binding sequences. In other amplification reactions, however, the amplification primers comprise specialized sequences and structures necessary for the amplification reaction to occur. For example, amplification primers for 3SR and NASBA comprise an RNA polymerase promoter near the 5' end. The promoter is appended to the target sequence and serves to drive the amplification reaction by directing transcription of multiple RNA copies of the target. Amplification primers for SDA comprise a recognition site for a restriction endonuclease near the 5' end. The restriction site is appended to the target sequence and becomes hemimodified and double-stranded during the amplification reaction. Nicking of the restriction site once it becomes double stranded drives the SDA reaction by allowing synthesis and displacement of multiple copies of the target by polymerase.

When the detector/amplification primer forms a mismatch with the target at or near it's 3' end, amplification efficiency is reduced and the accompanying reduction in signal upon detection of the extended detector/amplification primer (i.e., the amplification product or amplicon) indicates the presence or the identity of an SNP at the nucleotide position in the target where the diagnostic mismatch with the detector/ amplification primer occurred. If the detector/amplification primer is tagged with a label which produces a signal change when the detector/amplification primer has been extended (as discussed below), the extension products may be detected in real-time as amplification of the target occurs, thus eliminating the additional steps of post-amplification detection of extension products. In isothermal amplification reactions such as SDA, a single mismatch at N-1 or N-2 in the detector/amplification primer in general may provide more efficient allele discrimination than a single mismatch at the 3' terminus, Therefore, a 3' terminal mismatch is not preferred when the detector primer is an amplification primer for an isothermal amplification reaction. This is in contrast to the teaching of the prior art for temperature cycling amplification reactions, where a 3' terminal mismatch on the PCR amplification primer reportedly gave adequate allele discrimination (see Kwok, et al., supra). However, also in contrast to the teaching of the prior art for PCR, in the isothermal amplification methods of the present invention a mismatch on the detector/amplification primer at N-1, to N-4 and a complementary 3' terminal nucleotide results in excellent allele discrimination, particularly if the optional second nondiagnostic mismatch is included. This embodiment is therefore preferred for detector/amplification primers of the invention.

In an alternative preferred embodiment, the detector primer is used in an isothermal amplification reaction as a signal primer (also referred to as a detector probe) as taught in U.S. Pat. No. 5,547,861, the disclosure of which is hereby incorporated by reference. In the amplification reaction, the signal primer hybridizes to the target sequence downstream of an amplification primer such that extension of the amplification primer displaces the signal primer and its extension product. After extension, the signal primer includes the downstream sequence which is the hybridization site for the second amplification primer. The second amplification primer hybridizes to the extended signal primer and primes synthesis of its complementary strand. Production of these double-stranded secondary amplification products may be detected not only as an indication of the presence of the target sequence, but in the methods of the invention a signal primer which has the sequence characteristics of a detector primer (a detector/signal primer) also facilitates detection and/or identification of SNP's within the target sequence. In this embodiment, a diagnostic mismatch at either the 3' terminus (N) or at N-1 to N-4 provides excellent allele discrimination. Allele discrimination is further improved with the use of a second nondiagnostic mismatch as previously described, particularly when using longer detector primers where the difference in hybridization efficiency between matched and mismatched primers is small. This finding was unexpected, as a 3' terminal diagnostic mismatch alone produced poor allele discrimination in detector/ amplification primers. Use of a detector/signal primer in an isothermal amplification reaction also allows detection of extension products and analysis of SNPs in real-time (i.e., concurrently with amplification) when the detector/signal primer is labeled with a reporter group which produces a detectable change in the signal when the detector/signal primer is extended. Alternatively, the detector/signal primer may be used post-amplification or without amplifying the target for detection of SNPs. In this embodiment, the detector signal primer is hybridized to the target downstream from any primer which is extendible by polymerase such that extension of the second primer displaces the detector/signal primer and any detector/signal primer extension products which may be produced.

Applicants hypothesize that the different results obtained with a diagnostic mismatch at the 3' terminus of a detector/ signal primer as compared to a diagnostic mismatch at the 3' terminus of a detector/amplification primer may be at least partially due to a kinetic effect. If a signal primer is not efficiently extended on a target to which it is hybridized (e.g., when it contains mismatches), it will be quickly displaced from the template by extension of the upstream amplification primer. If the signal primer is efficiently extended, extension will occur before the signal primer is displaced from the target. That is, the upstream amplification primer (which is typically perfectly matched and efficiently extended) imposes a "time-limit" for extension on the detector/signal primer. In contrast, the amplification primer in an isothermal amplification reaction typically does not have a time-limit for extension imposed upon it by additional components of the isothermal amplification reaction or by thermocycling. Therefore, with sufficient time available, a detector/amplification primer may eventually be extended even when the extension reaction is inefficient. This phenomenon could reduce discrimination between alleles when a detector/amplification primer with a 3' terminal mismatch is employed in isothermal amplification reactions. However, a time limit may be imposed prior to amplification if a second primer binds upstream from the amplification primer, as described in U.S. Pat. No. 5,270,184 (e.g., the "external" or "bumper" primer). In this case, extension of the upstream primer places a time limit on extension of the amplification primer. If extension of the amplification primer is retarded by a mismatch at or near the 3' end, the amplification primer may be displaced by elongation of the upstream primer before it is extended. This kinetic effect is expected to enhance the ability of amplification primers to discriminate between matched and mismatched targets prior to amplification when there is an upstream primer to displace them. If mispriming occurs, however, the ability of amplification primers to correct a mismatch with the target may result in an amplification product which is not a faithful copy of the original target. Amplification primers produce amplicons that are perfectly matched with the amplification primers which produced them, thus eliminating the basis of allele discrimination. In contrast, such "correction" does not occur with signal primers.

Whether hybridization of the detector primer results in correct base-pairing or a mismatch at the diagnostic nucleotide position of the target being analyzed is determined by evaluating the relative efficiency of detector primer extension by DNA polymerase. This determination may be quantitative or qualitative. Detector primer extension is less efficient in the presence of a mismatch at or near the 3' end and more efficient when the entire 3' end is correctly base-paired with the target. That is, relatively more extended detector primer product is produced with correct base-pairing near the 3' terminus. The extended detector primer is typically detected by means of a label associated with the detector primer. The label may be directly detectable or detectable only after subsequent reaction as is known in the art. Alternatively, the detector primer itself may be unlabeled and the extension product detected by hybridization to a labeled probe or in a subsequent reaction such as treatment with ethidium bromide for visualization on a gel. The relative amount of signal from the label which is associated with the extended detector primer as compared to the amount of signal associated with the unextended primer serves as an indication of the amount of extension product produced and the efficiency of the extension reaction.

There are many techniques known in the art for determining the presence or amount of extended detector primer product produced in the amplification reaction. First, the extension products of the detector primer may be detected and/or quantified by their increased size, for example by separation from unextended detector primer by gel elecrophoresis or by selectively capturing the extended detector primer on a solid phase. However, in a preferred embodiment the detector primers are labeled with a reporter group which is detectable only when the detector primer has been extended or a label which produces a change in signal only when the detector primer has been extended. One example of such labels are fluorescent dyes which undergo changes in fluorescence polarization when the oligonucleotides to which they are linked have been hybridized to and extended on a target sequence. Methods employing changes in fluorescence polarization to detect hybridization and extension of a signal primer are described in U.S. Pat. No. 5,800,989; U.S. Pat. No. 5,593,867 and; U.S. Pat. No. 5,641,633. These patents describe using changes in fluorescence polarization which occur when the signal primer becomes double-stranded (made possible by its successful extension on the target sequence) to detect target amplification. In the methods of the invention, changes in fluorescence polarization of a fluorescently-labeled detector primer may be used to evaluate extension efficiency and to detect or identify an SNP in the target being amplified.

A second example of labels which undergo a detectable change in signal indicative of primer extension are fluorescent donor/quencher dye pairs. The quencher dye may also be fluorescent but need not be. When the donor and quencher are in close proximity, fluorescence of the donor is quenched. As the dyes are moved farther apart, quenching is reduced and donor fluorescence increases. The use of such donor/quencher dye pairs in a variety of mechanisms for increasing the distance between the dyes in the presence of target for detection of target nucleic acids is described in U.S. Pat. No. 5,846,726; U.S. Pat. No. 5,691,145, and; EP 0 881 302. Both the use of donor/quencher dye pairs in signal primer amplification systems and in extendible primer/probes for detection of unamplified or post-amplification targets are disclosed. In the present invention, the detector primers of the invention may be labeled with donor/quencher dye pairs and employed for detection and/or identification of SNP's in the target as is known in the art.

As disclosed in the foregoing references, a variety of primer extension detection systems are known for use in essentially any nucleic acid amplification reaction. They are particularly well-suited to isothermal amplification reactions where they provide rapid, real-time detection of primer extension. In the methods of the present invention, detector primers may be labeled with structures containing fluorescent reporter groups as taught in the foregoing references and the extension product detected by changes in fluorescence polarization or fluorescence quenching. Alternatively the detector primer may be unlabeled and its extension product detected by hybridization to a labeled primer/probe with detection of changes in fluorescence polarization or fluorescence quenching of the primer/probe as taught in these references.

EXAMPLE 1

To demonstrate identification of a single nucleotide polymorphism using labeled detector primers model target oligonucleotides differing by only a single nucleotide were prepared as follows: Four oligonucleotides containing identical sequences except at one position were synthesized. The variant position of the oligonucleotide contained either adenosine (A), cytosine (C), guanine (G) or thymine (T). A fifth oligonucleotide complementary to the 3' termini of the four variant oligonucleotides was also synthesized. Each of the four variant oligonucleotides was mixed with the fifth oligonucleotide, heated for 2 min. in a boiling water bath and equilibrated to 37° C. in a dry incubator. The annealed variant oligonucleotide and the fifth oligonucleotide were then extended in a primer extension reaction comprising 14 mM deoxycytidine α-(O-1-thio)-triphosphate, 2 mM deoxyadenosine triphosphate, 2 mM deoxyguanosine triphosphate, 2 mM thymidine triphosphate and 40 units of exonuclease deficient Klenow DNA polymerase. The primer extension reactions were allowed to proceed for 45 min. at 37° C., following which the Klenow polymerase was inactivated by incubating the reactions at 70° C. for 10 min. in a dry incubator. This produced four double-stranded DNA model target sequences differing only at one nucleotide position. The targets were designated A, C, G and T targets.

A second set of four oligonucleotides which hybridize to the model target sequences with their 3' termini at the polymorphic nucleotide position were also synthesized for use as detector primers. Each of the four detector primers had one of the four nucleotide bases (A, C, G or T) at its 3' terminus (N, the diagnostic nucleotide) and an "A" nucleotide at the position three bases from the 3' terminus which formed a mismatch with the model target sequence (N-3, the nondiagnostic nucleotide). The four detector primers were radiolabeled in 25 µl reactions containing 1 µM detector primer, 25 units of T4 polynucleotide kinase (PNK), 175 µCi of α-[$^{32}$P]-adenosine triphosphate ($^{32}$P-ATP), and PNK buffer at 1× concentration. Labeling reactions were initiated by addition of PNK to a solution containing the other components. The reactions were incubated for 20 min. at 37° C., than heated in a boiling water bath for 5 min. to inactivate the PNK.

The detector primers were used as signal primers in the amplification reaction. A 5 µl aliquot of each of the labeled detector primer preparation was added to a separate SDA reaction for each target (50 µl comprising 40 mM $KH_2PO_4$/

K$_2$HPO$_4$ pH 7.6; 10% v/v glycerol; 7.5 mM magnesium acetate; 0.5 μM each amplification primer; 1.4 mM deoxycytidine α-(O-1-thio)-triphosphate; 0.5 mM deoxyadenosine triphosphate; 0.5 mM deoxyguanosine triphosphate; 0.5 mM thymidine triphosphate; 0.1 mg/ml bovine serum albumin; 0.5 μg human placental DNA, 10$^4$ A, C, G or T target DNA molecules; 100 nM radiolabeled detector primer; 160 units BsoBi restriction endonuclease and 25 units Bst DNA polymerase large fragment). The SDA reactions were assembled without the BsoBI and Bst, and the target DNA duplexes were denatured by heating these reaction mixes for 3 min. in a boiling water bath. The reaction mixtures were equilibrated to 55° C. for 3 min. in a dry incubator and SDA was initiated by adding 160 units of BsoBI and 25 units of Bst polymerase large fragment to each reaction (total volume of enzymes was 2 μl, adjusted with 50% v/v glycerol). SDA was allowed to proceed for 30 min. at 55° C. Aliquots of each reaction (5 μl) were removed at 5 min. intervals during the reaction and added to 5 μl of sequencing stop solution to quench the SDA reaction. When all samples had been collected, they were incubated in a boiling water bath for 3 min. and 5 μl of each sample was loaded onto an 8% polyacrylamide, 7M urea sequencing gel. Following electrophoresis at 65 W for 50 min., the radiolabeled reaction products and unreacted probe on the gel were quantified by exposing a Molecular Dynamics Phosphorimager™ plate to the gel for 15 min. and reading the number of counts present in the radiolabeled product and probe bands on the Phosphorimager™ plate using ImageQuant™ software.

FIGS. 1A, 1B, 1C and 1D show the results obtained for extension of each of the four detector primers on each of the four different model target sequences. In each case, the detector primer with the 3' nucleotide that was the correct match for the polymorphic nucleotide in the target DNA sequence was preferentially extended during SDA by the DNA polymerase as compared to the detector primers which did not contain the correct 3' match for the polymorphic nucleotide in the target, as evidenced by greater amounts of the correct detector primer after amplification. For example, the 3'A detector primer was preferentially extended only in the SDA reactions containing the T target sequence (FIG. 1A). There was essentially no extension of the 3'A detector primer on the C, G or A target sequences. Extension products produced during SDA included full-length extended radiolabeled DNA probes and the nicked extended amplicons characteristic of SDA. Similarly, the T target supported little or no extension of the 3C, 3G and 3T detector primers (FIGS. 1B, 1C and 1D). Similar results were seen using each of the other detector primers in target amplification reactions (3C, 3G and 3T detector primers shown in FIGS. 1B, 1C and 1D, respectively), i.e., the detector primer was preferentially extended on the target which produced the correct 3' match at the polymorphic position in the target. In contrast, when an SDA amplification primer with a C at the 3' terminus was used as a detector/amplification primer in the amplification reactions the allele could not be identified (FIG. 1E). These results illustrate that N/N-3 detector/signal primers according to the invention can be used in isothermal amplification reactions to identify the nucleotide present at a selected position in a target nucleic acid sequence, whereas N/N-3 detector/amplification primers for isothermal amplification reactions do not effectively discriminate between alleles.

EXAMPLE 2

Example 1 was repeated except that the detector/signal primers were synthesized so that the variant, diagnostic nucleotide was positioned one nucleotide from the 3' terminus of the detector primer (N-1) and the overall length of the detector primer was shortened by 4 nucleotides at the 5' end. The detector primers also made a perfect match with the target DNA at the position three nucleotides from the 3' terminus of the detector primer. Each of the four detector primers was added to separate SDA reactions containing 10$^4$ molecules of each of the target sequences. The targets were amplified and detected as previously described. FIGS. 2A (–1A detector primer), 2B (–1C detector primer), 2C (–1G detector primer) and 2D (–1T detector primer) show the results of the experiments. In every case, during amplification the detector primer was preferentially extended on the target which contained the perfect match at the variant position. Signals obtained with the perfectly matched detector primer and target were 30- to 100-fold higher than signals obtained with any of the mismatched detector primer/target pairs. This difference in signal allowed unambiguous identification of the polymorphic nucleotide in the target and is in contrast to the results reported for PCR by Kwok, et al., supra, where an N-1 mismatch had no effect on the yield of PCR amplicons.

Similar results were obtained using a detector/signal primer having an N-1 diagnostic nucleotide (G) and a second nondiagnostic mismatch with the targets at N-2 (A). This detector primer was five nucleotides longer at the 5' end than the detector primers used in Example 1. The detector primer was added to each of four separate SDA reactions prepared as in Example 1, and was found to be preferentially extended on the target which contained the correct match for the diagnostic nucleotide (C). FIG. 2E shows that the signal obtained with the singly mismatched target was over five-fold higher than that obtained with any of the doubly mismatched targets and that the C allele could be easily distinguished from the T, G and A alleles of the target.

EXAMPLE 3

In the following experiments, a single nucleotide polymorphism in exon 4 of the HFE gene (the gene responsible for hemochromatosis) and the wild-type allele were detected and identified simultaneously in real-time during amplification using the detector primers of the invention. The wild-type allele is a G at nucleotide 845, whereas the mutant allele is an A at this position. This results in a cysteine to tyrosine change at amino acid position 282 in the protein.

SDA was generally performed as described in U.S. Pat. No. 5,846,726, except that each reaction mixture contained two detector/signal primers according to the invention (one specific for the mutant allele and one specific for the wild-type allele) and BsoBI was substituted for AvaI. The final concentrations of components in each 100 μL reaction were 50 mM KiPO$_4$ (pH 7.5), 6.0 mM MgOAc, 0.2 mM each dTTP, dGTP, dATP, 1.4 mM dCTPαS, 5 μg/mL acetylated BSA, 15% (v/v) glycerol, 400 ng salmon sperm DNA, 20 units exo Klenow Bst polymerase, 160 units BsoBI and either 0 or 10$^5$ copies of target DNA. In this example, target DNA consisted of PCR products generated from DNA cloned from either normal or mutant HFE exon 4 DNA. Normal HFE exon 4 DNA contains a G at nucleotide position 845 of the HFE wild-type gene and the mutant HFE exon 4 DNA contained an SNP at that position in which the nucleotide was A. Each sample also contained two detector/signal primers (SEQ ID NO:1 and SEQ ID NO:2 below), two unlabeled bumper primers (SEQ ID NO:3 and SEQ ID NO:4 below) and two unlabeled SDA amplification primers (SEQ ID NO:5 and SEQ ID NO:6 below). Underlined sequences indicate complementarity to the target sequence. The base A at position N-3 which is not underlined is not complementary to the corresponding nucleotide in the target sequence. This internal mismatch improves the selectivity of this detector primer for the nucleotide position 845. C* represents the 3' terminal nucleotide (position N of the detector primer) which pairs with the G at position 845 of the wild-type target. T* represents the 3' terminal nucleotide which pairs with A at nucleotide position 845 of the mutant target (the G845A mutation). Italicized sequences represent restriction enzyme recognition sites (RERS). In the amplification primers the RERS provides the nicking site which drives SDA. In the detector primers the RERS is flanked by a two dyes which form a donor/quencher dye pair. As the detector/signal primer is extended, displaced and rendered double-stranded the RERS also becomes double-stranded and cleavable by the restriction enzyme. To detect the amount of double-stranded extension product the reaction products are treated with the appropriate restriction enzyme to cleave the RERS of the detector primer. Quenching of the fluorescent dye decreases as the double-stranded products are cleaved and the dye pair is separated. The increase in fluorescence is an indicator of the amount of extended, double-stranded detector primer produced. If the detector primer is not efficiently extended the RERS remains single-stranded, is not cleaved by the restriction enzyme and the fluorescent dye remains quenched. Failure to detect an increase in fluorescence therefore indicates that the detector primer was not efficiently extended on the target.

SEQ ID NO:1—Detector primer specific for nucleotide G at position 845 (wild-type):
  FAM-TC CTC GAGT(dabcyl)A*TGGGTGCTCCACC* A GGC* (300 nM)

SEQ ID NO:2—Detector primer specific for nucleotide A at position 845 (mutant):
  Rox-TT CTC GAGT(dabcyl)TA CA TGGGTGCTCCACC AGGT* (300 nM)

SEQ ID NO:3—first bumper primer for exon 4:
  CGA ACC TAA AGA CGT ATT CGG C (50 nM)

SEQ ID NO:4—second bumper primer for exon 4:
  CCC CAA TAG ATT TTC TCA GCT CC (50 nM)

SEQ ID NO:5—first SDA amplification primer for exon 4:
  ACC GCA TCG ATT GCA TGT CTC GGG CTGGATACCCTTGGCT SEQ ID NO:6—second SDA amplification primer for exon 4:
  CGA TTC CGC TCC AGA CTT CTC GGG AGATCACMTGAGGGGCTGA Each SDA reaction included both detector primers, each labeled with a different fluorophore as shown above. The reactions were assembled in microwells to contain all reagents except Bst and BsoBI and amplification was initiated after heat denaturation and equilibration to 55° C. by addition of the enzymes. The microwells were sealed and placed into a Cytofluor II™ which had been modified to permit temperature control. Bandpass filters were used to limit excitation to one wavelength range characteristic of fluorescein (475-495 nm) and a second range specific for ROX (635-655 nm). For each well, one fluorescein and one ROX reading were made every 45 seconds. Reactions were typically monitored for 90 min. Control reactions contained no target DNA.

The results are shown in FIGS. 3A, 3B and 3C. In samples containing only targets derived from normal exon 4 DNA (FIG. 3A), fluorescence increased strongly with time in the emission wavelength range characteristic of fluorescein (FAM, 520-540 nm), indicating that the SEQ ID NO:1 detector primer was efficiently extended on this target and identifying the presence of the wild-type allele. In contrast, in the normal exon 4 samples emission fluorescence characteristic of ROX (635-655 nm) remained low, indicating that the SEQ ID NO:2 detector primer was not efficiently extended on the target during amplification and the confirming the absence of the mutant allele. In contrast, the fluorescence profile was reversed for samples containing DNA derived from mutant exon 4 DNA and lacking normal DNA (FIG. 3B). In these samples, fluorescence increased strongly at the emission wavelengths of ROX but not at FAM wavelengths, indicating the presence of the mutant allele and the absence of the wild-type allele. In the sample containing both wild-type and mutant DNA, fluorescence increased in both monitored ranges, indicating the presence of both alleles in the sample (FIG. 3C).

In a similar experiment, an alternative detector primer specific for the wild type allele was tested and its performance compared to the SEQ ID NO:1 detector primer. The alternative detector primer had a diagnostic nucleotide at N-2 and a second nondiagnostic nucleotide at N-3 (an N-2/N-3 detector primer; FAM-TC CTC GAG T(dabcyl)A TGGGTGCTCCACCTGA C*AC; SEQ ID NO: 14). In addition, amplification primer SEQ ID NO:5 was replaced with SEQ ID NO:15 (ACG CAG CAG CAC ACA TTC TCG GGGMGAGCAGAGATATACGT) Two samples were tested using SEQ ID NO:14—one containing only wild type target and the other containing only mutant target. Each test reaction contained SEQ ID NO:14 for detection of the wild type allele and SEQ ID NO:2 for detection of the mutant target. The SEQ ID NO:1/SEQ ID NO:2 detector primer system served as a control reaction. Both fluorescein and rhodamine fluorsense were monitored and the fluorescence readings for each sample were plotted. In the sample containing the wild-type target, the N-2/N-3 detector primer was converted, resulting in a three-fold increase in fluorescein emission. The mutant-specific detector primer remained unconverted and the rhodamine emission was essentially unchanged. In the sample containing only mutant target, the pattern was reversed. The N-2/N-3 detector primer was not converted, as indicated by no change in fluorescein emission, but rhodamine emission from the mutant-specific detector primer increased about three-fold. Comparison of the results to the control reaction demonstrated that the target specificity for SEQ ID NO:14 is approximately equivalent to the target specificity for SEQ ID NO:1.

It has also been found that a wild-type specific detector primer having the sequence FAM-TA GCA GTC CCGAGA CTG CT(dabcyl)A TGGGTGCTCCACCAGGC* (SEQ ID NO:16) provides more sensitive detection of the wild-type allele than SEQ ID NO:1, although it is slightly less specific.

EXAMPLE 4

The experimental protocol of Example 3 was repeated except that a pair of amplification primers specific for exon 2 of the HFE gene and detector/signal primers for detection and identification of wild-type and mutant alleles in exon 2 were used. The wild-type allele is C at nucleotide 187. The mutant allele has a G in this position, resulting in a histidine to lysine change at amino acid 63 in the protein. These detector primers were designed to hybridize to the allele contained in the non-coding strand of exon 2.

SEQ ID NO:7—Detector primer for wild-type allele at nucleotide position 187 (C187, i.e., G on the complementary strand):

FAM-TC CTC GAGT(dabcyl)T
ACCAGCTGTTCGTGTTCTATGATC* (300 nM)
SEQ ID NO:7—Detector primer for mutant allele at nucleotide position 187 (G187, i.e., C on the complementary strand):
Rox-TA CCG CAC T(dabcyl)GA TT
ACCAGCTGTTCGTGTTCTATAATG* (300 nM)
SEQ ID NO:9—First bumper primer for exon 2:
TGA ACA TGT GAT CCC ACC CT (50 nM)
SEQ ID NO:10—Second bumper primer for exon 2:
CCC CM TAG ATT TTC TCA GCT CC (50 nM)
SEQ ID NO:11—First amplification primer for SDA:
ACC GCA TCG MT GCA TGT CTCGGG
AGCTTTGGGCTACGTGGATG
SEQ ID NO:12—Second amplification primer for SDA:
CGA TTC CGC TCC AGA CTT CTC GGG
GCTCCACACGGCGACTCT SEQ ID NO:7 did not contain a nondiagnostic mismatch with the target. SEQ ID NO:8 did not contain an RERS, as the ROX/Dabcyl dye pair dequenches upon formation of the extended, double-stranded detector primer product. Cleavage with a restriction enzyme is not necessary to observe the increase in fluorescence.

The results are shown in FIGS. 4A, 4B and 4C for SDA reactions containing $10^7$ copies of target DNA derived from either wild-type or mutant exon 2. In samples containing target derived from normal exon 2 DNA only (FIG. 4A), fluorescence increased strongly with time in the emission wavelength range for fluorescein, indicating the presence of the wild-type allele. In addition, fluorescence in the emission wavelength range for rhodamine remained low for these samples, indicating the absence of the mutant allele. In contrast, the fluorescence profile was reversed for samples containing DNA derived only from mutant exon 2 (FIG. 4B). In this case, ROX fluorescence increased strongly and FAM fluorescence remained low. In samples containing both wild-type and mutant DNA (FIG. 4C), fluorescence from both fluorophores increased strongly, indicating the presence of both alleles in a single sample.

In addition, it has been found that substituting an amplification primer having the sequence CGA TAC GCT CCT GAC TTC TCG GGA CAA ACGGCGACTCTCAT (SEQ ID NO:17) for SEQ ID NO:12 in the reaction provides more efficient amplification of the exon 2 target. Further, an N-1 detector primer having the sequence Rox-TA GCG CCC GAG CGC T(dabcyl)ATGTTCGTGTTCTATGATC*A (SEQ ID NO:18) provides improved allele discrimination when used in combination with the alternative amplification primer SEQ ID NO:17.

EXAMPLE 5

This example illustrates the use of 5' tail sequences in detector primers to modulate cross-reactivity of multiple allele-specific probes in nucleic acid amplification reactions. Although this example employed SDA, similar results are expected for other amplification methods known in the art, including PCR, NASBA, 3SR, etc., which involve extension of a labeled probe or primer to discriminate between two alleles.

Examples 3 and 4 describe SDA reactions which contain two differentially labeled detector/signal primers, one specific for the wild-type allele and the other specific for a mutant allele. Thus, each reaction mixture is capable of detecting either the mutant allele, the wild-type allele or both alleles simultaneously. The ability to analyze one sample for either allele is more convenient and reliable, requires less sample and is less expensive than the alternative approach of splitting the sample sample and performing two separate single-detector primer assays. However, it has been observed that in reaction mixtures containing two or more differentially-labeled detector primers an increased level of spurious, cross-reactive signal may be generated by one detector primer when the target of a second detector primer is present. Applicants believe that this cross-reactivity is caused or exacerbated by the simultaneous presence of both detector primers in the same reaction mixture, as cross-reactivity is diminished or absent in single-detector primer reaction mixtures. It has been discovered that the cross-reactivity can be substantially diminished in such multiple detector primer reaction mixtures by designing detector primers so that the 5' tail sequences of the two detector primers are substantially different. This result was unexpected, as the 5' tails are not complementary to the original target sequences and the allele-specific nucleotides are located away from the 5' tails at or near the 3' ends of the detector primers.

FIG. 5 illustrates the possible source of this unexpected cross-reactivity, using SDA as an illustrative example. The "wild-type" target depicted contains a C at the nucleotide position to be diagnosed. The detector primer for this allele therefore contains a 3' terminal G, as shown. For purposes of this illustration, the "mutant" allele (not shown) contains a T at the diagnostic position, and its detector primer contains a 3' terminal A. Both detector primers are present in the amplification reaction. During amplification, the C-specific detector primer hybridizes to the target and is extended and converted to the double-stranded form which is cleavable to separate the donor/quencher dye pair. The resulting increase in fluorescence indicates the presence of the C-containing target. The remaining double-stranded species then undergoes linear amplification, as this species contains a nickable restriction site. Linear amplification produces a single-stranded species containing a C at the diagnostic position. Two alternative reaction pathways are then possible. In one case, the linear amplification product may hybridize to the appropriate C-specific detector primer and be converted to cleaved product as before, further enhancing the C-specific signal. Alternatively, the linear amplification reaction product may hybridize spuriously to the T-specific detector primer. T the single mismatch at the 3' end of the T-specific detector primer would not be sufficient to prevent such errant hybridization. However, if the 5' tail sequences of the T-specific and C-specific detector primers are identical hybridization could occur and the spuriously-hybridized T-specific detector primer would be converted quickly into a cleaved fluorescent product without the need for extension of the A:C mismatch. This results in a signal falsely indicative of the presence of a T nucleotide at the diagnostic position. If, however, the T-specific and C-specific detector primers contain different 5' tail sequences, spuriously hybridized T-specific detector primer will not undergo cleavage, as the 5' tail cannot be converted to double-stranded form by hybridization to the linear amplification product. The detector primer would then remain uncleaved even if errantly hybridized to wild-type target and no false-positive signal would be produced. In the illustrated example, the fact that the two detector primers have the same restriction site would not be sufficient to allow the tails to hybridize provided the rest of the 5' tail sequence was different.

Although FIG. 5 illustrates a mechanism for spurious generation of false-positive signals in SDA, similar reactions will occur in other amplification methods. Each time a single-stranded C-containing detector primer extension product is generated in PCR, NASBA, 3SR, TMA or any other amplification reaction, it may hybridize to either the C-specific detector primer (correctly) or to the T-specific detector primer (incorrectly). If the two detector primers have identical 5' tail sequences the extension product will be complementary to either one at its 5' end and the RERS will be double-stranded and cleavable. If the two detector primers have different 5' tail sequences the double-stranded RERS will not be generated when the detector primer hybridizes to the incorrect target and no false-positive signal will be generated.

To illustrate this phenomenon, four SDA reactions were assembled. All reactions contained the mutant-specific detector primer SEQ ID NO:2 (300 nM). Reactions 1 and 2 contained wild type-specific SEQ ID NO:13 (FAM-TT CTC GAG T(dabcyl)TA CATGGGTGCTCCACC AGGC* (300 nM), which has a 5' tail sequence identical to SEQ ID NO:2. Reactions 3 and 4 contained the fluorescein-labeled wild type-specific detector primer SEQ ID NO:1 (300 nM) in which the 5' tail sequence differs from SEQ ID NO:2 except for the RERS (CTCGAG). The reaction mixtures also contained either wild-type (reactions 1 and 3) or mutant (reactions 2 and 4) target DNA ($10^5$ copies per reaction) derived from exon 4 of the HFE gene (see Example 3). The reactions were carried out as in Example 3 except that only fluorescein fluorescence emissions were detected.

The results are shown in FIG. 6. Reaction 1 produced a strong increase in fluorescein fluorescence, indicative of the presence of the wild-type allele in the target. Reaction 2, which contained mutant DNA only, produced a diminished but substantial fluorescence increase even though no wild-type DNA was present. This signal represented spurious conversion of the wild-type "specific" detector primer, possibly through the mechanism illustrated in FIG. 5, as the 5' tail sequences of the two detector primers present in the reaction were identical. When the 5' tail sequence of the wild-type detector primer was changed (SEQ ID NO:1), the cross-reacting signal was suppressed (reaction 4) without substantially affecting the target-specific signal (reaction 3).

What is claimed is:

1. A method for detecting a single nucleotide polymorphism in a target comprising, under isothermal conditions at about 37 degrees Celsius:
   a) hybridizing a detector primer and a second primer to the target such that extension of the second primer by polymerase displaces the detector primer from the target sequence, wherein the detector primer comprises a diagnostic nucleotide for the single nucleotide polymorphism which is one to four nucleotides from the 3' terminal nucleotide of the detection primer;
   b) extending the detector primer and the second primer with polymerase to produce a displaced detector primer extension product;
   c) determining an efficiency of detector primer extension; and
   d) detecting the presence or absence of the single nucleotide polymorphism based on the efficiency of detector primer extension.

2. The method of claim 1 wherein the single nucleotide polymorphism is identified using the detector primer.

3. The method of claim 2 wherein the single nucleotide polymorphism is identified using multiple detector primers, each comprising a different diagnostic nucleotide.

4. The method of claim 3 wherein two detector primers are used to identify which of two possible alleles is present in the target sequence.

5. The method of claim 3 wherein four detector primers are used to identify the nucleotide present in the target sequence at the position of the single nucleotide polymorphism.

6. The method of claim 3 wherein each of the multiple detector primers has a different 5' tail sequence.

7. The method of claim 1 wherein the detector primer further comprises a nucleotide which forms a nondiagnostic mismatch with the target sequence.

8. The method of claim 7 wherein the nondiagnostic nucleotide is positioned within fifteen nucleotides of the diagnostic nucleotide in the detector primer.

9. The method of claim 8 wherein the nondiagnostic nucleotide is positioned 1-5 nucleotides from the diagnostic nucleotide in the detector primer.

10. The method of claim 9 wherein the nondiagnostic nucleotide is adjacent to the diagnostic nucleotide in the detector primer.

11. The method of claim 7 wherein the detector primer is about 15-36 nucleotides long.

12. The method of claim 11 wherein the detector primer is about 18-24 nucleotides long.

13. The method of claim 1 wherein the second primer is an amplification primer.

14. The method of claim 13 wherein the amplification reaction is selected from the group consisting of SDA, 3SR, NASBA, and TMA.

15. The method of claim 1 wherein the detector primer is about 12-50 nucleotides long.

16. The method of claim 15 wherein the detector primer is about 12-24 nucleotides long.

17. The method of claim 16 wherein the detector primer is about 12-19 nucleotides long.

18. The method of claim 1 wherein the presence or absence of the single nucleotide polymorphism is detected by means of a label associated with the detector primer.

19. The method of claim 18 wherein the label becomes detectable upon extension of the detector primer or produces a change in signal upon extension of the detector primer.

20. The method of claim 19 wherein the label is a fluorescent donor/quencher dye pair and an increase in donor dye fluorescence is detected as an indication of the presence of the single nucleotide polymorphism.

21. The method of claim 19 wherein a change in fluorescence polarization is detected as an indication of the presence of the single nucleotide polymorphism.

22. The method of claim 1 wherein a single nucleotide polymorphism in an HFE gene is detected.

23. The method of claim 22 wherein the single nucleotide polymorphism is detected in exon 4 or exon 2 of the HFE gene.

24. The method of claim 1 wherein the efficiency of detector primer extension is determined quantitatively.

25. A method for detecting a single nucleotide polymorphism in a target comprising, in an isothermal nucleic acid amplification reaction at about 37 degrees Celsius:
   a) hybridizing a detector primer to the target, wherein the detector primer comprises a diagnostic nucleotide for the single nucleotide polymorphism one to four nucleotides from a 3' terminal nucleotide of the detector primer which is complementary to the target sequence;
   b) amplifying the target by hybridization and extension of the detector primer;
   c) determining an efficiency of detector primer extension, and;
   d) detecting the presence or absence of the single nucleotide polymorphism based on the efficiency of detector primer extension.

26. The method of claim 25 wherein the single nucleotide polymorphism is identified using the detector primer.

27. The method of claim 26 wherein the single nucleotide polymorphism is identified using two or more detector primers, each comprising a different diagnostic nucleotide.

28. The method of claim 27 wherein two detector primers are used to identify which of two possible alleles is present in the target sequence.

29. The method of claim 27 wherein four detector primers are used to identify the nucleotide present in the target sequence at the position of the single nucleotide polymorphism.

30. The method of claim 27 wherein each of the multiple detector primers has a different 5' tail sequence.

31. The method of claim 25 wherein the detector primer further comprises a nucleotide which forms a nondiagnostic mismatch with the target sequence.

32. The method of claim 31 wherein the nondiagnostic nucleotide is positioned within fifteen nucleotides of the diagnostic nucleotide in the detector primer.

33. The method of claim 32 wherein the nondiagnostic nucleotide is positioned 1-5 nucleotides from the diagnostic nucleotide in the detector primer.

34. The method of claim 33 wherein the nondiagnostic nucleotide is adjacent to the diagnostic nucleotide in the detector primer.

35. The method of claim 31 wherein the detector primer is about 15-36 nucleotides long.

36. The method of claim 35 wherein the detector primer is about 18-24 nucleotides long.

37. The method of claim 25 wherein the isothermal amplification reaction is selected from the group consisting of SDA, 3SR, NASBA and TMA.

38. The method of claim 25 wherein the detector primer is about 12-50 nucleotides long.

39. The method of claim 38 wherein the detector primer is about 12-24 nucleotides long.

40. The method of claim 39 wherein the detector primer is about 12-19 nucleotides long.

41. The method of claim 25 wherein the presence or absence of the single nucleotide polymorphism is detected by means of a label associated with the detector primer.

42. The method of claim 41 wherein the label becomes detectable upon extension of the detector primer or produces a change in signal upon extension of the detector primer.

43. The method of claim 42 wherein the label is a fluorescent donor/quencher dye pair and a decrease in donor dye fluorescence is detected as an indication of the presence of the single nucleotide polymorphism.

44. The method of claim 42 wherein a change in fluorescence polarization is detected as an indication of the presence of the single nucleotide polymorphism.

45. The method of claim 25 wherein the efficiency of detector primer extension is determined quantitatively.

46. The method of claim 25 further comprising, prior to amplifying, displacing the hybridized detector primer from the target by extension of an upstream primer.

47. A method for detecting a single nucleotide polymorphism in a target sequence comprising, under isothermal conditions at about 37 degrees Celsius:
   a) hybridizing to the target sequence a detector primer comprising a diagnostic nucleotide for the single nucleotide polymorphism which is one to four nucleotides from the 3' terminal nucleotide of the detection primer;
   b) in a primer extension reaction, displacing the detector primer by extension of a second primer hybridized to the target sequence upstream of the detector primer, and;
   c) detecting the presence or absence of the single nucleotide polymorphism based on an efficiency of detector primer extension.

48. The method of claim 47 wherein the single nucleotide polymorphism is identified using the detector primer.

49. The method of claim 48 wherein the single nucleotide polymorphism is identified using multiple detector primers, each detector primer comprising a different diagnostic nucleotide.

50. The method of claim 49 wherein each of the multiple detector primers comprises a different 5' tail sequence.

51. The method of claim 47 wherein the second primer is an amplification primer.

52. The method of claim 47 wherein the detector primer comprises a label which becomes detectable upon extension of the detector primer or which produces a change in signal upon extension of the detector primer.

53. The method of claim 52 wherein the label is a fluorescent donor/quencher dye pair and a decrease in donor dye fluorescence is detected as an indication of the presence or absence of the single nucleotide polymorphism.

54. A method for detecting a single nucleotide polymorphism in a target comprising, under isothermal conditions at about 37 degrees Celsius:
  a) hybridizing a detector primer and a second primer to the target such that extension of the second primer by polymerase displaces the detector primer from the target sequence, wherein the detector primer comprises a diagnostic nucleotide for the single nucleotide polymorphism which is two to four nucleotides from the 3' terminal nucleotide of the detection primer;
  b) extending the detector primer and the second primer with polymerase to produce a displaced detector primer extension product;
  c) determining an efficiency of detector primer extension, and;
  d) detecting the presence or absence of the single nucleotide polymorphism based on the efficiency of detector primer extension.

* * * * *

SEQUENCE LISTING

<160> NUMBER OF SEQ ID NOS: 18

<210> SEQ ID NO 1
<211> LENGTH: 27
<212> TYPE: DNA
<213> ORGANISM: Homo sapiens

<400> SEQUENCE: 1
tcctcgagta tgggtgctcc accaggc                                        27

<210> SEQ ID NO 2
<211> LENGTH: 30
<212> TYPE: DNA
<213> ORGANISM: Homo sapiens

<400> SEQUENCE: 2
ttctcgagtt acatgggtgc tccaccaggt                                     30

<210> SEQ ID NO 3
<211> LENGTH: 22
<212> TYPE: DNA
<213> ORGANISM: Homo sapiens

<400> SEQUENCE: 3
cgaacctaaa gacgtattcg gc                                             22

<210> SEQ ID NO 4
<211> LENGTH: 23
<212> TYPE: DNA
<213> ORGANISM: Homo sapiens

<400> SEQUENCE: 4
ccccaataga ttttctcagc tcc                                            23

<210> SEQ ID NO 5
<211> LENGTH: 40
<212> TYPE: DNA
<213> ORGANISM: Homo sapiens

<400> SEQUENCE: 5
accgcatcga ttgcatgtct cgggctggat acccttggct                          40

```
<210> SEQ ID NO 6
<211> LENGTH: 44
<212> TYPE: DNA
<213> ORGANISM: Homo sapiens

<400> SEQUENCE: 6
cgattccgct ccagacttct cgggagatca caatgagggg ctga              44

<210> SEQ ID NO 7
<211> LENGTH: 34
<212> TYPE: DNA
<213> ORGANISM: Homo sapiens

<400> SEQUENCE: 7
tcctcgagtt accagctgtt cgtgttctat gatc                         34

<210> SEQ ID NO 8
<211> LENGTH: 37
<212> TYPE: DNA
<213> ORGANISM: Homo sapiens

<400> SEQUENCE: 8
taccgcactg attaccagct gttcgtgttc tataatg                      37

<210> SEQ ID NO 9
<211> LENGTH: 20
<212> TYPE: DNA
<213> ORGANISM: Homo sapiens

<400> SEQUENCE: 9
tgaacatgtg atcccaccct                                         20

<210> SEQ ID NO 10
<211> LENGTH: 23
<212> TYPE: DNA
<213> ORGANISM: Homo sapiens

<400> SEQUENCE: 10
ccccaataga ttttctcagc tcc                                     23

<210> SEQ ID NO 11
<211> LENGTH: 44
<212> TYPE: DNA
<213> ORGANISM: Homo sapiens

<400> SEQUENCE: 11
accgcatcga atgcatgtct cgggagcttt gggctacgtg gatg              44

<210> SEQ ID NO 12
<211> LENGTH: 42
<212> TYPE: DNA
<213> ORGANISM: Homo sapiens

<400> SEQUENCE: 12
cgattccgct ccagacttct cggggctcca cacggcgact ct                42

<210> SEQ ID NO 13
<211> LENGTH: 30
<212> TYPE: DNA
<213> ORGANISM: Homo sapiens

<400> SEQUENCE: 13
```

-continued

```
ttctcgagtt acatgggtgc tccaccaggc                                          30

<210> SEQ ID NO 14
<211> LENGTH: 29
<212> TYPE: DNA
<213> ORGANISM: Homo sapiens

<400> SEQUENCE: 14
tcctcgagta tgggtgctcc acctgacac                                           29

<210> SEQ ID NO 15
<211> LENGTH: 42
<212> TYPE: DNA
<213> ORGANISM: Homo sapiens

<400> SEQUENCE: 15
acgcagcagc acacattctc ggggaagagc agagatatac gt                            42

<210> SEQ ID NO 16
<211> LENGTH: 37
<212> TYPE: DNA
<213> ORGANISM: Homo sapiens

<400> SEQUENCE: 16
tagcagtccc gagactgcta tgggtgctcc accaggc                                  37

<210> SEQ ID NO 17
<211> LENGTH: 41
<212> TYPE: DNA
<213> ORGANISM: Homo sapiens

<400> SEQUENCE: 17
cgatacgctc ctgacttctc gggacaaacg gcgactctca t                             41

<210> SEQ ID NO 18
<211> LENGTH: 35
<212> TYPE: DNA
<213> ORGANISM: Homo sapiens

<400> SEQUENCE: 18
tagcgcccga gcgctatgtt cgtgttctat gatca                                    35
```